United States Patent
Micallef et al.

(10) Patent No.: US 9,187,780 B2
(45) Date of Patent: Nov. 17, 2015

(54) METHOD FOR DETECTING NUCLEOSOME ADDUCTS

(71) Applicant: Singapore Volition Pte Limited, Singapore (SG)

(72) Inventors: Jacob Vincent Micallef, London (GB); Mark Edward Eccleston, London (GB); Marielle Herzog, London (GB)

(73) Assignee: Singapore Volition Pte. Limited, Singapore (SG)

( * ) Notice: Subject to any disclaimer, the term of this patent is extended or adjusted under 35 U.S.C. 154(b) by 0 days.

(21) Appl. No.: 14/362,596

(22) PCT Filed: Dec. 7, 2012

(86) PCT No.: PCT/GB2012/053057
§ 371 (c)(1),
(2) Date: Jun. 3, 2014

(87) PCT Pub. No.: WO2013/084002
PCT Pub. Date: Jun. 13, 2013

(65) Prior Publication Data
US 2014/0322719 A1 Oct. 30, 2014

(30) Foreign Application Priority Data

Dec. 7, 2011 (GB) .................................... 1121040.8
Dec. 12, 2011 (GB) .................................... 1121230.5

(51) Int. Cl.
*G01N 33/53* (2006.01)
*C12Q 1/68* (2006.01)
*G01N 33/574* (2006.01)
*G01N 33/68* (2006.01)

(52) U.S. Cl.
CPC ........ *C12Q 1/6804* (2013.01); *G01N 33/57488* (2013.01); *G01N 33/57496* (2013.01); *G01N 33/6875* (2013.01); *G01N 2800/52* (2013.01); *G01N 2800/56* (2013.01)

(58) Field of Classification Search
None
See application file for complete search history.

(56) References Cited

FOREIGN PATENT DOCUMENTS

| EP | 1 668 368 | 6/2006 |
|---|---|---|
| FR | 2 652 901 | 4/1991 |
| WO | WO-01/53834 | 7/2001 |
| WO | WO-2005/019826 | 3/2005 |
| WO | WO-2005/040814 | 5/2005 |
| WO | WO-2007/076200 | 7/2007 |
| WO | WO-2011/131772 | 10/2011 |
| WO | WO-2011/157905 | 12/2011 |

OTHER PUBLICATIONS

Andersson, Ulf, and Harris, Helena Erlandsson, "The role of HMGB1 in the pathogenesis of rheumatic disease", Biochimica et Biophysica Acta, 1799., pp. 141-148, 2010.
Fullgrabe et al., "Histone onco-modifications", Oncogene, 30(31), pp. 3391-3403, 2011.
Urbonaviciute, et al., "Induction of inflammatory and immune responses by HMGB1-nucleosome complexes: implication for the pathogenesis of SLE", J. Exp. Med., 205(13), pp. 3007-3018, 2008.
Urbonaviciute, V. and Voll, R.E., "High-mobility group box 1 represents a potential marker of disease activity and novel therapeutic target in systemic lupus erythematosus", J. Internal Medicine,vol. 270, pp. 1365-2796, 2011.

*Primary Examiner* — Jacob Cheu
(74) *Attorney, Agent, or Firm* — Foley & Lardner LLP

(57) ABSTRACT

The invention relates to a method for detecting and measuring the presence of nucleosome-protein adducts and the use of such measurements for the detection and diagnosis of disease. The invention also relates to a method of identifying nucleosome adduct biomarkers for the detection and diagnosis of disease and to biomarkers identified by said method.

21 Claims, 11 Drawing Sheets

METHOD FOR DETECTING NUCLEOSOME ADDUCTS

FIELD OF THE INVENTION

The invention relates to a method for detecting and measuring the presence of nucleosome-protein adducts and the use of such measurements for the detection and diagnosis of disease. The invention also relates to a method of identifying nucleosome adduct biomarkers for the detection and diagnosis of disease and to biomarkers identified by said method.

BACKGROUND OF THE INVENTION

The human body comprises several hundred cell types. All of these cell types contain the same genome but widely different phenotypes and different functions in the body. This phenotypic diversity is due to the differential expression of the genome in different cell types. The control of differential gene expression is not entirely understood but the basic mechanisms include gene regulation by a number of interconnected epigenetic signals associated with the gene, including control of the chromatin packing as euchromatin or heterochromatin, control of nucleosome positioning and nuclease accessible sites, methylation of DNA and variation in the structure of the nucleosomes around which the DNA is wrapped.

The nucleosome is the basic unit of chromatin structure and consists of a protein complex of eight highly conserved core histones (comprising of a pair of each of the histones H2A, H2B, H3, and H4). Around this complex is wrapped approximately 146 base pairs of DNA. Another histone, H1 or H5, acts as a linker and is involved in chromatin compaction. The DNA is wound around consecutive nucleosomes in a structure often said to resemble "beads on a string" and this forms the basic structure of open or euchromatin. In compacted or heterochromatin this string is coiled and super coiled into a closed and complex structure (Herranz and Esteller, 2007).

Normal cell turnover in adult humans involves the creation by cell division of some $10^{11}$ cells daily and the death of a similar number, mainly by apoptosis. During the process of apoptosis chromatin is broken down into mononucleosomes and oligonucleosomes which are released from the cells. Under normal condition these are removed and the level of circulating nucleosomes found in healthy subjects is low. Elevated levels are found in subjects with a variety of conditions including many cancers, auto-immune diseases, inflammatory conditions, stroke and myocardial infarction (Holdenrieder & Stieber, 2009).

Mononucleosomes and oligonucleosomes can be detected by Enzyme-Linked ImmunoSorbant Assay (ELISA) and several methods have been reported (Salgame et al, 1997; Holdenrieder et al, 2001; van Nieuwenhuijze et al, 2003). These assays typically employ an anti-histone antibody (for example anti-H2B, anti-H3 or anti-H1, H2A, H2B, H3 and H4) as capture antibody and an anti-DNA or anti-H2A-H2B-DNA complex antibody as detection antibody. However, we have found that the results of these assays do not agree with each other. Furthermore, although most circulating DNA in serum or plasma is reported to exist as mono-nucleosomes and oligo-nucleosomes (Holdenrieder et al, 2001), measured levels of nucleosomes and DNA in serum or plasma do not agree well. The correlation coefficient between ELISA results for circulating cell free nucleosomes levels and circulating DNA levels as measured by real time PCR (Polymerase Chain Reaction) has been reported to be r=0.531 in serum and r=0.350 in plasma (Holdenrieder et al, 2005).

Nucleosome ELISA methods are used in cell culture, primarily as a method to detect apoptosis (Salgame et al, 1997; Holdenrieder et al, 2001; van Nieuwenhuijze et al, 2003), and are also used for the measurement of circulating cell free nucleosomes in serum and plasma (Holdenrieder et al, 2001). Cell free serum and plasma nucleosome levels released into the circulation by dying cells have been measured by ELISA methods in studies of a number of different cancers to evaluate their use as a potential biomarker (Holdenrieder et al, 2001). Mean circulating nucleosome levels are reported to be high in most, but not all, cancers studied. The highest circulating nucleosome levels were observed in lung cancer subjects. The lowest levels were observed in prostate cancer, which were within the normal range of healthy subjects. However, subjects with malignant tumours are reported to have serum nucleosome concentrations that varied considerably and some subjects with advanced tumour disease were found to have low circulating nucleosome levels, within the range measured for healthy subjects (Holdenrieder et al, 2001). Because of this and the variety of non-cancer causes of raised nucleosome levels, circulating nucleosome levels are not used clinically as a biomarker of cancer (Holdenrieder and Stieber, 2009).

The structure of nucleosomes can vary by Post Transcriptional Modification (PTM) of histone proteins and by the inclusion of variant histone proteins. PTM of histone proteins typically occurs on the tails of the eight core histones and common modifications include acetylation, methylation or ubiquitination of lysine residues as well as methylation of arginine residues and phosphorylation of serine residues. Histone modifications are known to be involved in epigenetic regulation of gene expression (Herranz and Esteller, 2007). The structure of the nucleosome can also vary by the inclusion of alternative histone isoforms or variants which are different gene or splice products and have different amino acid sequences. Histone variants can be classed into a number of families which are subdivided into individual types. The nucleotide sequences of a large number of histone variants are known and publicly available for example in the National Human Genome Research Institute NHGRI Histone Data-Base (Mariño-Ramirez, L., Levine, K. M., Morales, M., Zhang, S., Moreland, R. T., Baxevanis, A. D., and Landsman, D. The Histone Database: an integrated resource for histones and histone fold-containing proteins. Database Vol. 2011. (Submitted) and http://genome.nhgri.nih.gov/histones/complete.shtml), the GenBank (NIH genetic sequence) DataBase, the EMBL Nucleotide Sequence Database and the DNA Data Bank of Japan (DDBJ).

Histone variant and histone modification patterns present in healthy and diseased cells have been shown to differ in numerous (mostly immunohistochemical) studies (Herranz and Esteller, 2007). One disadvantage of immunohistochemical methods for clinical use is that tissue sample collection is invasive involving surgery or biopsy.

In addition to the epigenetic signaling mediated by nucleosome structure and position, control of gene expression in cells is also mediated by the methylation status of DNA (Herranz and Esteller, 2007). It has been known in the art for some time that DNA may be methylated at the 5 position of cytosine nucleotides to form 5-methylcytosine.

The involvement of DNA methylation in cancer was reported as early as 1983 (Feinberg and Vogelstein, 1983). DNA methylation patterns observed in cancer cells differ from those of healthy cells. Repetitive elements, particularly around pericentromeric areas, are reported to be hypomethylated in cancer relative to healthy cells but promoters of specific genes are reported to be hypermethylated in cancer. The balance of these two effects is reported to result in global DNA hypomethylation in cancer cells (Rodriguez-Paredes & Esteller, 2011).

Hypermethylation of certain specific genes can be used as a diagnostic biomarker for cancers. For example a method reported for detection of hypermethylation of the Septin 9 gene by PCR amplification of DNA extracted from plasma was reported to detect 72% of colon cancers with a false positive rate of 10% (Grutzmann et al, 2008). The DNA methylation status of specific genes or loci is usually detected by selective bisulphite deamination of cytosine, but not 5-methylcytosine, to uracil, leading to a primary DNA sequence change that can be detected by sequencing or other means (Allen et al, 2004).

Global DNA hypomethylation is a hallmark of cancer cells (Esteller 2007 and Hervouet et al, 2010). Global DNA methylation can be studied in cells using immunohistochemistry techniques. Alternatively the DNA is extracted from the cells for analysis.

It has been known for many years that, in addition to nucleic acid and histone proteins, chromatin comprises a large number of non-histone proteins bound to its constituent DNA and/or histones (Yoshida and Shimura, 1972). These chromatin associated proteins are of a wide variety of types and have a variety of functions including transcription factors, transcription enhancement factors, transcription repression factors, histone modifying enzymes, DNA damage repair proteins and many more. The study of chromatin bound proteins has been carried out largely by Chromatin Immuno-Precipitation (ChIP) methods. These methods are well known in the art but are complex, laborious and expensive.

In a typical ChIP method the cellular chromatin is cross-linked so that all the protein and nucleic acid components are covalently attached to each other. The chromatin is then sheared to form a preparation of mononucleosomes and oligonucleosomes. An antibody to the protein of interest is added to the sheared chromatin to immunoprecipitate those chromatin fragments containing the protein. The antibody is normally attached to a solid phase (eg; plastic beads) to facilitate isolation of the chromatin complex containing the protein of interest. The cross-linking is then reversed and the protein is removed by digestion with a proteinase. The DNA associated with the chromatin complex is isolated and analysed to determine the DNA sequence, gene or locus associated with the particular protein binding using any of a variety of techniques including PCR followed by gel electrophoresis, DNA sequencing (ChIP-Seq) or DNA microarrays (ChIP-on-chip).

These ChIP methods reveal the DNA sequences associated with chromatin bound histone proteins. Derivatives of the ChIP method have been developed to facilitate studies of the association of non-histone proteins with histones and nucleosomes including for example Histone Associated Assays (Ricke and Bielinsky, 2005). Many proteins that bind to chromatin are involved in cancer and other disease mechanisms but their abundance in nucleosome adduct form in the circulation has not been previously investigated. Examples include the High Mobility Group Box Protein 1 (HMGB1), the polycomb protein Enhancer of Zeste Homolog 2 (EZH2) and the nuclear receptor group of proteins.

The High Mobility Group of proteins are a component of chromatin present at about 3% of the weight of DNA or histones. They are structural proteins that bind to nucleosomes without any known specificity for the underlying DNA sequence (Gerlitz et al; 2009). HMGB1 is an architectural chromosomal protein and a pro-inflammatory mediator. It is involved in cell death, apoptosis and in numerous diseases including various inflammatory and autoimmune conditions, sepsis, meningitis and neurodegeneration. Overexpression of HMGB1 is associated with all of the central hallmarks of cancer (Tang et al; 2010). HMGB1 is tightly attached to the chromatin of apoptotic cells. Studies of nucleosome-HMGB1 complexes have shown that these adducts are found in the circulation of subjects suffering from the autoimmune disease Systemic Lupus Erythematosus (SLE) and that the adducts are involved in the development of anti-nuclear antibodies which is a key feature of SLE. Nucleosomes not attached to HMGB1 do not illicit an immune response. The binding of HMGB1 to nucleosomes in these adducts was demonstrated by immunoprecipitation of nucleosomes with an antibody directed to DNA or histones followed by Western Blot using an anti-HMGB1 antibody to demonstrate the presence of HMGB1 in the immunoprecipitated nucleosomes (Urbonaviciute et al; 2008).

HMGB proteins interact with many other proteins known to affect chromatin function and chromatin complexes involving HMGB proteins plus additional proteins have been shown to occur (Gerlitz et al; 2009). Thus, in addition to simple nucleosome-protein adducts, nucleosome-protein-complex adducts in which 2 or multiple proteins are associated with nucleosomes occur in chromatin.

EZH2 is a member of the Polycomb-group (PcG) family that form multimeric protein complexes involved in maintaining the transcriptional repressive state of genes. EZH2 is a histone modification enzyme (histone-lysine N-methyltransferase) that methylates the lysine 27 amino acid residue of histone 3 of nucleosomes. This histone modification is associated with chromatin condensation and gene silencing (Cao et al; 2002).

Nuclear receptors are molecules that regulate gene expression under the control of hormones or ligands, for example the estrogen receptor (ER) regulates the expression of estrogen dependent genes. Many of these proteins are involved in disease processes, for example ER is involved in the progression of breast cancer and many breast cancer treatments are targeted to ER and/or to prevention of the interaction of ER with its ligand estradiol.

In addition to nucleosome-protein adducts that occur in the cell, there are other nucleosome-protein adducts that may be formed after release of nucleosomes from the cell following cell death. Such nucleosome adducts include the nucleosome-immunoglobulin adducts that are a key feature of SLE.

We now report simple immunoassay methods for the direct estimation of protein-nucleosome adducts in biological samples. We have developed simple methods for the detection of nucleosome bound EZH2, HMGB1 and several nuclear receptors and shown that such nucleosome adducts can be detected in serum samples and that they have use as biomarkers in disease.

SUMMARY OF THE INVENTION

According to a first aspect of the invention there is provided the use of a nucleosome-protein adduct as a biomarker in blood for the diagnosis of cancer, autoimmune disease or inflammatory disease.

According to a second aspect of the invention there is provided a method for detecting the presence of a nucleosome-protein adduct in a sample which comprises the steps of:

(i) contacting the sample with a first binding agent which binds to nucleosomes or a component thereof;

(ii) contacting the nucleosomes or sample with a second binding agent which binds to a protein adducted to a nucleosome;
(iii) detecting or quantifying the binding of said second binding agent to the adducted protein in the sample; and
(iv) using the presence or degree of such binding as a measure of the presence of nucleosome adducts in the sample.

According to a third aspect of the invention there is provided a method for detecting the presence of a nucleosome adduct in a sample which comprises the steps of:
(i) contacting a sample with a first binding agent which binds to a protein adducted to a nucleosome;
(ii) contacting the nucleosomes or sample with a second binding agent which binds to nucleosomes or a component thereof;
(iii) detecting or quantifying the binding of said second binding agent to nucleosomes or a component thereof in the sample; and
(iv) using the presence or degree of such binding as a measure of the presence of nucleosome adducts in the sample.

According to a further aspect of the invention there is provided a method for detecting a nucleosome adduct in a cell which comprises the steps of:
(i) isolating chromatin from a cell;
(ii) digesting, sonicating or otherwise breaking down the chromatin to form mono-nucleosomes and/or oligo-nucleosomes; and
(iii) detecting or measuring the presence of the nucleosome adduct according to an ELISA method of the invention described in the above second or third aspects.

According to a further aspect of the invention there is provided a method for detecting or diagnosing a disease status in an animal or a human subject which comprises the steps of:
(i) detecting or measuring a nucleosome adduct in a body fluid of a subject; and
(ii) using the nucleosome adduct level detected to identify the disease status of the subject.

According to a further aspect of the invention there is provided a method for assessment of an animal or a human subject for suitability for a medical treatment which comprises the steps of:
(i) detecting or measuring a nucleosome adduct in a body fluid of the subject; and
(ii) using the nucleosome adduct level detected as a parameter for selection of a suitable treatment for the subject.

According to a further aspect of the invention there is provided a method for monitoring a treatment of an animal or a human subject which comprises the steps of:
(i) detecting or measuring a nucleosome adduct in a body fluid of the subject;
(ii) repeating the detection or measurement of a nucleosome adduct in a body fluid of the subject on one or more occasions;
(iii) using any changes in the nucleosome adduct level detected as a parameter for any changes in the condition of the subject.

According to a further aspect of the invention there is provided a method for identifying a nucleosome adduct biomarker for detecting or diagnosing a disease status in an animal or a human subject which comprises the steps of:
(i) detecting or measuring a nucleosome adduct in a body fluid of the subject;
(ii) detecting or measuring a nucleosome adduct in a body fluid of a healthy subject or a control subject; and
(iii) using the difference between the levels detected in diseased and control subjects to identify whether a nucleosome adduct is useful as a biomarker for the disease status.

According to a further aspect of the invention there is provided a biomarker identified in accordance with methods defined herein.

According to a further aspect of the invention there is provided a kit for the detection of a nucleosome adduct which comprises a ligand or binder specific for the nucleosome adduct or component part thereof, or a structural/shape mimic of the DNA base, nucleotide or nucleoside or component part thereof, together with instructions for use of the kit.

DETAILED DESCRIPTION OF THE INVENTION

Figure 1:
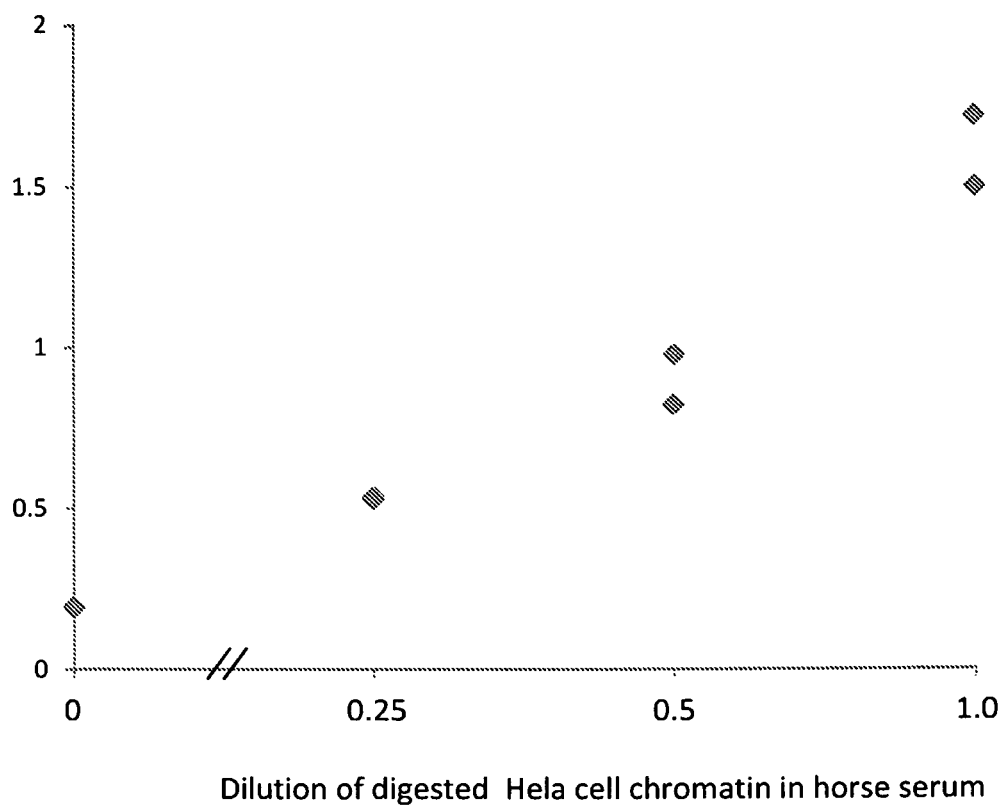
FIG. 1: ELISA dose response curve for the detection of nucleosome EZH2 adduct levels in digested chromatin extracted from Hela cells diluted into horse serum.

According to a first aspect of the invention there is provided the use of a nucleosome-protein adduct as a biomarker in blood for the diagnosis of cancer, autoimmune disease or inflammatory disease. In one embodiment, the biomarker is used for the diagnosis of cancer. We have shown that two such adducts containing HMGB1 and EZH2 are present in the circulation of subjects with cancer but are not detected in the circulation of healthy subjects.

It is well known in the art that cancers may be hormone dependent and require the presence of hormone for growth. It is also well known that nuclear hormones function by nuclear localisation of the receptor bound hormone complex and binding to specific hormone response elements in the genome. The expression of genes associated with the elements is regulated by binding of the receptor bound hormone complex to the genomic response element. In one embodiment the invention provides hormone receptor-nucleosome adduct and hormone-hormone receptor-nucleosome complex adduct biomarkers to characterise the tumour status of a subject. These adducts may be circulating adducts present in the blood or in another body fluid or may be produced by the digestion of chromatin from a sample of tumour tissue.

It is well known in the art that nuclear hormone receptors regulate gene expression under hormonal or ligand control. For example the estrogen receptor functions by binding its substrate (the steroid hormone estrogen) at the cell surface membrane. Binding is followed by internalisation of the hormone-receptor complex and intra-nuclear localisation where the receptor binds to specific hormone response elements in the genome. The specific gene sequence to which the estrogen receptor binds is known as the Estrogen Response Element (ERE). Expression of genes associated with the ERE may be regulated by the receptor and hence by the presence or level of estrogen in the circulation of a subject. It is also well known in the art that growth of breast cancer is often under estrogen control and such cancer is often termed estrogen dependent. As these tumours over express the Estrogen Receptor (ER) they are often termed ER+ tumours. The growth of estrogen dependent tumours can be slowed or prevented by therapeutic interventions aimed at prevention of estrogen binding to the estrogen receptor and this is a common method of breast cancer treatment. Examples of such treatments include the drug Tamoxifen which acts as an antagonist for estrogen in estrogen dependent breast cancer and aromatase inhibitors which slow or prevent estrogen production. However, with time, cancers develop into estrogen independent tumours which will grow even in the absence of estrogen stimulation and require different treatments. The diagnosis of estrogen dependent and independent tumours is currently performed routinely by immunostaining of tumour biopsy tissue to determine the abundance or otherwise of the estrogen receptor in tumour cells. Clinicians may need to retest the estrogen dependency of a tumour repeatedly during the course of tumour treatment to determine whether or not further estrogen dependent treatment is appropriate or whether the subject's treatment regime should be altered to reflect the changing nature of the tumour as the disease progresses. Unfortunately current tests are suboptimal and require repeated painful biopsy on each occasion the test is performed. In one embodiment of the invention the detection of estrogen receptor-nucleosome adducts in the circulation of breast cancer patients is used as an indicator of estrogen receptor binding to ERE in the nucleus of tumour cells as an indicator for estrogen dependency of a tumour to aid the selection of appropriate treatment and for predictive prognostic information. This method has the advantages that it is indicative of ERE-estrogen receptor binding in the tumour, rather than a simple indicator of the presence or abundance of estrogen receptor, and that it may be repeated as frequently as desired by a simple blood test without the need for biopsy. We have developed simple ELISA methods for the detection and quantification of nucleosome-ER adducts containing both the ERα and ERβ forms of the receptor. Surprisingly these adducts are present in the circulation of cancer patients.

It will be clear to those skilled in the art that the same principle can be applied to the detection of estrogen receptor-nucleosome adducts in cell chromatin digests produced from the tumour tissue itself. This method for assessing the estrogen dependency of a tumour is superior to current methods because it is indicative of ERE-estrogen receptor binding in the tumour, rather than a simple indicator of the presence or abundance of estrogen receptor.

In another embodiment of the invention the detection of the presence of steroid estrogen itself in an estrogen-estrogen receptor-nucleosome complex adduct either in the circulation, or in another body fluid, or in nucleosomes produced as a digest of chromatin from tumour tissue is used as an indicator of estrogen dependency status of a tumour.

It is reported that circulating nucleosomes are elevated in endometriosis (Holdenrieder et al; 2001) and, as endometriosis tissue is estrogen responsive, binding of the estrogen receptor in the chromatin of endometriosis cells may lead to estrogen receptor-nucleosome adducts or estrogen-estrogen receptor-nucleosome complex adducts in the circulation. In a further embodiment of the invention estrogen receptor-nucleosome adducts or estrogen-estrogen receptor-nucleosome complex adducts are detected in a body fluid as a biomarker for the presence of an estrogen dependent gynaecological condition including for example endometriosis.

In a similar manner to estrogen dependent breast cancer, the growth of androgen dependent prostate cancer requires, or is accelerated by androgen. Androgen dependent prostate tumours are similarly treated by methods that prevent androgen binding to the androgen receptor (AR). Androgen dependent prostate tumours may also develop to become androgen independent and hence resistant to treatments including physical or chemical castration by drugs to prevent androgen binding to its receptor. The androgen dependency status of a tumour may be determined by the level of androgen receptor binding to androgen response elements (ARE) in the genome and this may be determined by the analysis of androgen receptor-nucleosome adduct levels present in the circulation of a subject or in chromatin digests from prostate tissue. Embodiments of the invention for this purpose include the detection of androgen receptor-nucleosome adducts or androgen-androgen receptor-nucleosome complex adducts in the circulation or in a body fluid of a subject or in nucleosomes produced by digestion of chromatin from tumour tissue of a subject. We have now developed simple ELISA methods for the detection and quantification of nucleosome-AR adducts and demonstrated their utility. We have also developed simple ELISA methods for the detection and quantification of nucleosome-Progesterone Receptor adducts. Other hormone dependent diseases may be addressed with similar embodiments of the method of the invention. Such embodiments include the detection of other receptor-nucleosome adducts including for example glucocorticoid receptor, thyroid hormone receptor and retinoic acid receptor-nucleosome adducts for the detection of tumours including for example various types of leukaemia involving the retinoic acid receptor.

According to a further aspect of the invention, the methods described hereinbefore may be used to detect hormone-hormone receptor-nucleosome complex adducts. In one embodiment, the hormone-hormone receptor-nucleosome complex adducts comprise a thyroxine-thyroid hormone receptor-nucleosome complex adduct, a triiodothyronine-thyroid hormone receptor-nucleosome complex adduct, a retinoic acid-retinoic acid receptor-nucleosome complex adduct, an androgen-androgen receptor-nucleosome complex adduct or an estrogen-estrogen receptor-nucleosome complex adduct. This aspect of the invention has the advantage of distinguishing hormone activated adducts as well as adducts containing wild type or normal hormone receptor from hormone receptor which does not bind its ligand, for example due to mutation in the course of disease progression (for example in estrogen independent breast cancer). This aspect of the invention may be carried out in multiple ways. In one embodiment an antibody or other binder directed to bind to the hormone itself is used in place of the antibody directed to bind the hormone receptor. In an alternative embodiment hormone is extracted from an antibody captured hormone-hormone receptor-nucleosome complex adduct and quantified by established methods for example immunoassay methods, spectrographic methods or chromatographic methods including high performance liquid chromatography (HPLC), liquid chromatography followed by mass spectroscopy (LC/MS) or gas chromatography followed by mass spectroscopy (GC/MS). For example, androgen-androgen receptor-nucleosome complex adduct is captured by immobilised antibodies directed to bind to an epitope present on the adduct (for example on the androgen receptor or on a nucleosome). The hormone is then extracted from the solid phase bound adduct into an organic solvent (for example; diethyl ether). The solvent is transferred, dried and the androgen is redissolved in assay buffer and its concentration is measured (for example by competitive immunoassay). It will be clear to those skilled in the art that this embodiment will have particular application for small molecule hormones such as steroid and thyroid hormones.

The present invention is aimed at detection of proteins which are bound to nucleosomes. This can be done by means of a double antibody ELISA test in which one antibody is directed to bind nucleosomes and the other is directed to bind to the protein bound to the nucleosome. However the antibody directed to bind to the nucleosome need not be directed to the whole nucleosome complex but may be directed to a protein or nucleic acid component part of the nucleosome. In this embodiment of the invention the antibody employed to bind to the nucleosome may be directed to bind any component part of a nucleosome including, for example to a particular histone, histone modification, histone variant or isoform or to a particular nucleotide or modified nucleotide. We have shown that this design of assay works well using the example of using an antibody directed to bind to the histone variant H2AZ as a binder of nucleosomes. It will be clear to those skilled in the art that this method has the additional advantage of selectively binding only those nucleosomes which contain both the protein of interest in the adduct and H2AZ. This design provides a method for an assay to test for any combination of adduct protein with any particular histone, histone modification, histone variant, nucleotide, modified nucleotide or other nucleosome structure.

According to a second aspect of the invention there is provided a method for detecting the presence of a nucleosome-protein adduct in a sample which comprises the steps of:
(i) contacting the sample with a first binding agent which binds to nucleosomes or a component thereof;
(ii) contacting the nucleosomes or sample with a second binding agent which binds to a protein adducted to a nucleosome;
(iii) detecting or quantifying the binding of said second binding agent to the adducted protein in the sample; and
(iv) using the presence or degree of such binding as a measure of the presence of nucleosome adducts in the sample.

It will be clear to those skilled in the art that the binding agent to be detected may be selected to be either the antibody directed to the adducted protein or to the nucleosome or a component part of the nucleosome.

According to a third aspect of the invention there is provided a method for detecting the presence of a nucleosome adduct in a sample which comprises the steps of:
(i) contacting a sample with a first binding agent which binds to a protein adducted to a nucleosome;
(ii) contacting the nucleosomes or sample with a second binding agent which binds to nucleosomes or a component thereof;
(iii) detecting or quantifying the binding of said second binding agent to nucleosomes or a component thereof in the sample; and
(iv) using the presence or degree of such binding as a measure of the presence of nucleosome adducts in the sample.

In one embodiment, the nucleosome adduct includes a pro-inflammatory protein, a High Mobility Group Protein, a polycomb protein, a chromatin modifying enzyme, a nuclear receptor or a hormone. In an alternative embodiment, the nucleosome adduct includes a High Mobility Group Protein, a polycomb protein, a chromatin modifying enzyme, a hormone receptor or a hormone. In a further embodiment, the nucleosome adduct includes a chromatin modifying enzyme, a nuclear receptor or a hormone. In a further embodiment, the High Mobility Group Protein is HMGB1. In one embodiment, when the biomarker is used for the diagnosis of cancer, the nucleosome-protein adduct includes a High Mobility Group Protein.

In one embodiment, the chromatin modifying enzyme is a histone acetylation, deacetylation, methylation, demethylation phosphorylation, dephosphorylation ubiquitination, deubiquitination sumoylation, desumoylation or DNA methyltransferase enzyme. In an alternative embodiment, the chromatin modifying enzyme is EZH2.

In one embodiment, when the nucleosome-protein adduct includes a nuclear receptor, said nuclear receptor is the estrogen receptor, androgen receptor, progesterone receptor, thyroid hormone receptor, glucocorticoid receptor or retinoic acid receptor. In an alternative embodiment, when the nucleosome-protein adduct includes a nuclear receptor, said nuclear receptor is the estrogen receptor, androgen receptor or retinoic acid receptor.

In one embodiment, when the nucleosome-protein adduct includes a hormone, said hormone is a thyroid hormone, a glucocorticoid hormone or a steroid hormone including an estrogen, an androgen, a progestogen, a corticosteroid or retinoic acid. In an alternative embodiment, when the nucleosome-protein adduct includes a hormone, said hormone is a steroid hormone including an estrogen, an androgen, a corticosteroid or retinoic acid.

In one embodiment, when the nucleosome-protein adduct includes a hormone receptor, said hormone receptor is the estrogen receptor, androgen receptor, progesterone receptor, thyroid hormone receptor or retinoic acid receptor.

We have shown that the method can be performed using an antibody directed to the nucleosome itself in combination with an antibody directed to bind to the protein adducted to the nucleosome or using an antibody directed to a component of a nucleosome, again in combination with an antibody directed to bind to the protein adducted to the nucleosome. In one embodiment, the nucleosome or nucleosome component antibody or binder is directed to bind a particular epigenetic nucleosome epitope; for example any histone variant (eg; H2AZ), any histone modification (eg; trimethyl H3K9) or any nucleotide or modified nucleotide (eg; 5-methylcytosine). In an alternative embodiment, the nucleosome or nucleosome component binder is directed to bind to a particular epigenetic signal structure such that only a particular subset of nucleosome adducts containing said epigenetic signal structure are detected.

In one embodiment, the binding agent used is an antibody, an antibody fragment or an aptamer. In a further embodiment, the binding agent used is an antibody.

In one embodiment, the sample is a biological fluid. In a further embodiment, the sample is blood or serum or plasma. It will be clear to those skilled in the art that the detection of nucleosome adducts in a body fluid has the advantage of being a minimally invasive method that does not require biopsy.

In some cases however, it may be preferable to assess the nucleosome adduct status of a cell directly by producing nucleosomes from that cell and analyzing the nucleosomes for the presence of particular nucleosome adducts.

According to a further aspect of the invention there is provided a method for detecting a nucleosome adduct in a cell which comprises the steps of:
  (i) isolating chromatin from a cell;
  (ii) digesting, sonicating or otherwise breaking down the chromatin to form mono-nucleosomes and/or oligo-nucleosomes; and
  (iii) detecting or measuring the presence of the nucleosome adduct according to an ELISA method of the invention described in any of the above second to sixth aspects.

According to a further aspect of the invention there is provided a method for detecting or diagnosing a disease status in an animal or a human subject which comprises the steps of:
  (i) detecting or measuring a nucleosome adduct in a body fluid of a subject; and
  (ii) using the nucleosome adduct level detected to identify the disease status of the subject.

In one embodiment of the invention the presence of a nucleosome adduct in a sample is used to determine the optimal treatment regime for a subject in need of such treatment. One example of such an embodiment is the detection of a nuclear hormone receptor-nucleosome adduct or a hormone-hormone receptor-nucleosome complex adduct for assessment of the hormone dependency of a tumour.

According to a further aspect of the invention there is provided a method for assessment of an animal or a human subject for suitability for a medical treatment which comprises the steps of:
  (i) detecting or measuring a nucleosome adduct in a body fluid of the subject; and
  (ii) using the nucleosome adduct level detected as a parameter for selection of a suitable treatment for the subject.

According to a further aspect of the invention there is provided a method for monitoring a treatment of an animal or a human subject which comprises the steps of:
  (i) detecting or measuring a nucleosome adduct in a body fluid of the subject;
  (ii) repeating the detection or measurement of a nucleosome adduct in a body fluid of the subject on one or more occasions;
  (iii) using any changes in the nucleosome adduct level detected as a parameter for any changes in the condition of the subject.

In one embodiment, the nucleosome adduct is detected or measured as one of a panel of measurements.

According to a further aspect of the invention there is provided a method for detecting or measuring a nucleosome adduct, either alone or as part of a panel of measurements; for the purposes of detecting or diagnosing a disease status, or for assessment of an animal or a human subject for suitability for a medical treatment, or for monitoring a treatment of an animal or a human subject, for use in subjects with actual or suspected cancer, benign tumours, inflammatory disease, autoimmune disease, endometriosis, infectious disease, sepsis, stroke or myocardial infarction.

According to a further aspect of the invention there is provided a method for identifying a nucleosome adduct biomarker for detecting or diagnosing a disease status in an animal or a human subject which comprises the steps of:
  (i) detecting or measuring a nucleosome adduct in a body fluid of the subject;
  (ii) detecting or measuring a nucleosome adduct in a body fluid of a healthy subject or a control subject; and
  (iii) using the difference between the levels detected in diseased and control subjects to identify whether a nucleosome adduct is useful as a biomarker for the disease status.

According to a further aspect of the invention there is provided a kit for the detection of a nucleosome adduct which comprises a ligand or binder specific for the nucleosome adduct or component part thereof, or a structural/shape mimic of the DNA base, nucleotide or nucleoside or component part thereof, together with instructions for use of the kit.

In addition to histone and nucleic acid components, chromatin is known to contain a wide variety of proteins that perform a wide range of functions. We selected HMGB1, EZH2 and several nuclear receptors as examples of these proteins and have developed simple ELISA methods for the detection of mononucleosome and oligonucleosome adducts of these proteins. We performed these ELISA methods directly on serum samples taken from healthy and diseased subjects and the methods require no sample extraction or other sample pre-treatment. Surprisingly we have shown that these nucleosome adducts can be detected in the serum of cancer subjects and that nucleosome adduct ELISA assays are useful in the detection and diagnosis of disease states.

HMGB1 is a damage associated molecular pattern (DAMP) protein associated with cell death, apoptosis and numerous diseases including various inflammatory and autoimmune conditions, sepsis, meningitis, neurodegeneration, SLE and cancer (Tang et al; 2010). Elevated expression of HMGB1 occurs in many cancers and is thought to be associated with invasion and metastases (Sims et al, 2010). Elevated levels of HMGB1 also occur in the blood of cancer patients as well as in a variety of other conditions (Stoetzer et al, 2012). Circulating HMGB1 can be measured by ELISA but such measurements are not used in routine clinical practice because circulating HMGB1 occurs in bound and free forms and the Western immunoblot methods currently available to distinguish these are not suitable for routine use. Therefore there is a need for a reliable method to distinguish between free HMGB1 and HMGB1 complexes (Urbonaviciute and Voll, 2011). An important class of circulating HMGB1 complexes is HMGB1-nucleosome adducts and one embodiment of the present invention is directed to the detection of HMGB1-nucleosome adducts and other HMG-nucleosome adducts. We have shown that HMG-nucleosome adducts can be measured in the blood of cancer patients using a rapid and simple ELISA method.

HMGB1 is tightly attached to the chromatin of apoptotic cells. Studies of nucleosome-HMGB1 complexes have shown that these adducts are found in the circulation of subjects suffering from the autoimmune disease SLE and that the adducts are involved in the development of anti-nuclear antibodies which is a key feature of SLE. The presence of these adducts in the circulation has not been used for clinical diagnostic purposes because the Western blot methods used for their detection are expensive, slow and laborious and not suitable for routine clinical use. The present invention overcomes these shortcomings.

EZH2 is a chromatin modification enzyme (histone-lysine N-methyltransferase) that methylates the lysine 27 amino acid residue of histone 3 of nucleosomes leading to chromatin condensation and gene silencing (Cao et al; 2002). This protein is known to bind chromatin in the nucleus of living cells. Surprisingly we have shown that EZH2 remains bound to nucleosomes after cell death and mononucleosome-EZH2 and oligonucleosome-EZH2 adducts can be detected in the serum of cancer subjects using the novel ELISA methods of the present invention.

It is known that chromatin modifying enzymes are involved in cancer (Fullgrabe et al, 2011) and inhibition of the activity of these enzymes through the use of targeted drugs is a major form of cancer therapy. These drugs include for example and without limitation Histone Deacetylation Complex inhibitors (HDACi), Histone Methyl Transferase inhibitors (HMTi) and DNA Methyl Transferase inhibitors (DNMTi). Whilst the presence of HMGB1 adducts in the circulation is known to be pathological and associated with anti-nuclear antibodies, the finding that chromatin modifying enzyme-nucleosome adducts are present in the circulation has not previously been reported. Assays for chromatin modifying enzyme-nucleosome adducts have multiple uses in cancer including for example in the assessment of cancer disease states and in the determination of the efficacy of chromatin modifying enzyme inhibitor drugs, for example to determine if the level of circulating chromatin modifying enzyme-nucleosome adduct is altered by treatment with particular drugs. The method of the invention may be used to determine circulating chromatin modifying enzyme-nucleosome adduct levels for a wide variety of disease diagnostic purposes including disease detection, monitoring, prognosis, differential diagnosis and choice of treatment regimes. We have shown that nucleosome adducts containing the HMT enzyme EZH2 can be detected in the circulation of cancer patients. It will be clear to those skilled in the art that the method of the invention may be applied to other chromatin modifying enzymes including the before mentioned HDAC and DNMT enzymes as well as many other enzymes including for example enzymes for histone acetylation, demethylation, phosphorylation, dephosphorylation, ubiquitination, deubiquitination, sumoylation and desumoylation.

Nuclear receptors exert their gene regulatory effects in the nucleus under ligand hormone control. Examples include the steroid hormone receptors, thyroid receptor, glucocorticoid receptor and retinoic acid and vitamin D receptor. These receptors are involved in a variety of cancer and other disease mechanisms. Some examples include the involvement of the Retinoic Acid Receptor (RAR) in leukaemia, the Estrogen Receptor (ER) in breast cancer and endometriosis, the Androgen Receptor (AR) in prostate cancer and the Thyroid Hormone Receptor in thyroid disease and cancer.

Surprisingly we have shown that nuclear receptor-nucleosome adducts can be detected in the circulation of cancer patients.

Thus all of the intra-cellular chromatin associated proteins we chose to study can be found in the serum of cancer patients in the form of nucleosome adducts. These findings indicate that such adducts may not be unusual and that many such intra-cellular nucleosome protein adducts, involving many different chromatin associated proteins, may retain their integrity following cell death and be amenable to detection in the serum of cancer, auto-immune and inflammatory disease patients by the method of the present invention.

We have used an anti-histone antibody as capture antibody for these assays in combination with an appropriate specific anti-chromatin protein (anti-HMGB1, anti-EZH2 or anti-nuclear receptor) antibody. We have used the assays to show that nucleosome adducts containing specific proteins can be measured in blood samples taken from subjects with cancer and are discriminating for use as non-invasive or minimally invasive biomarkers. The nucleosome-adduct levels detected in serum samples taken from diseased subjects differed from those detected in serum samples from healthy subjects.

We measured the levels of circulating cell free nucleosome-HMGB1 and nucleosome-EZH2 adducts in blood samples taken from 3 subjects with colon cancer, 6 subjects with lung cancer and 2 subjects with pancreatic cancer and compared these with the levels present in blood samples from 5 healthy subjects as well as with an artificially produced preparation of serum nucleosomes from healthy subjects prepared as described in the literature (*Holdenrieder et al, 2001) and with a commercially available preparation of nucleosomes prepared by digestion of chromatin extracted from Hela cells.

Normal ranges were calculated from the results for the 5 healthy subjects (mean result±2 standard deviations of the mean) for the nucleosome-HMBG1 and nucleosome-EZH2 adducts and the results for cancer subjects were examined to see if they fall within, or outside of, the respective normal range. The data show that 2 of 3 colon cancer samples, 4 of 6 lung cancer samples and 1 of 2 pancreatic cancer samples had elevated nucleosome-HMBG1 adduct levels and similarly that 2 of 3 colon cancer samples, 4 of 6 lung cancer samples and 1 of 2 pancreatic cancer samples had elevated nucleosome-EZH2 adduct levels (Optical Density results higher than the top of the normal range).

We have similarly measured the levels of nuclear receptor-nucleosome adducts in healthy and diseased patients and shown that these are present in the serum of cancer patients.

Proteins that bind to chromatin include, without limitation, nuclear receptors, the High Mobility Group proteins (such as HMGB1), polycomb proteins, chromatin modification enzymes (such as EZH2), DNA modification enzymes, nuclear receptors, transcription factors, architectural or structural proteins, transcription enhancement factors, transcription repression factors, replication proteins, DNA damage repair proteins and any other proteins involved in the control of gene expression, chromatin packing or replication.

Nucleosome adducts can also occur due to binding of nucleosomes present in a biological fluid after cell death. An example of such an adduct would be a nucleosome-antibody adduct formed an autoimmune disease such as SLE.

Thus in one embodiment of the invention there is provided a method for detecting or measuring the presence of a nucleosome-protein complex or adduct. The nucleosome adducts to be measured may be of any origin including, without limitation, naturally occurring nucleosome adducts present in biological fluids as a consequence of a healthy or diseased condition or nucleosome adducts may be produced by the digestion of chromatin extracted from cells, or they may be produced by induced apoptosis or necrosis of cells (for example by the method of *Holdenrieder et al; 2001). Surprisingly, we have shown that nucleosome adducts occur in all these situations and can be detected by the method of the invention.

In another embodiment of the invention there is provided a method for detecting or measuring the presence of a nucleosome-protein adduct in a biological fluid.

In a further embodiment of the invention there is provided a method for detecting or diagnosing the presence, type, recurrence or severity of a disease or assessing optimal drug or other treatment options by testing a subject sample for the presence or level of one or more nucleosome-protein complexes or adducts.

In a further embodiment of the invention there is provided a method for detecting or diagnosing the presence, type, recurrence or severity of a disease or assessing optimal drug or other treatment options by testing a sample taken from a subject for the presence or level of a nucleosome-protein complex or adduct as part of a panel of tests. An ELISA method for the detection of cell free nucleosomes containing different histone modifications has been reported (Bawden et al; 2005).

Thus, such a panel of tests may consist, for example, of two or more measurements of nucleosomes containing different nucleosome epitopes; including without limitation different adducts and/or histone modifications and/or histone variants and/or modified nucleotides and/or measurements of nucleosomes per se, or any combination or ratio of any of these and any other nucleosome epitopes, as an indicator of the health or disease status of a subject.

We conclude that the method of the present invention is a successful method for the detection and measurement of nucleosome adducts containing particular proteins, and that this method is a superior method for the detection of nucleosome adducts than the methods of the current art. The method is rapid, low cost and suitable for use in complex biological media and fluids including blood and its derivatives. We have demonstrated that the method of the current invention can be used to detect nucleosome adducts in blood, and that this may be used as a biomarker for cancer. It will be clear to those skilled in the art that a biomarker present in the blood has value for a broad range of diagnostic and disease screening purposes for cancer and other diseases which are associated with elevated circulating nucleosomes (Holdenrieder et al, 2001).

According to one aspect of the invention there is provided a double antibody, immunometric or sandwich immunoassay method for detecting and measuring cell free nucleosome adducts in a sample. One embodiment of this aspect is an immunoassay which comprises the steps of:
  (i) contacting a sample which may contain nucleosome adducts with a first antibody or other binder which binds to nucleosomes or a component thereof;
  (ii) contacting the nucleosomes or sample with a second antibody or other binder which binds to a protein that may be present as a nucleosome-protein adduct;
  (iii) detecting and/or quantifying the binding of said second antibody or other binder to a nucleosome-protein adduct in the sample; and
  (iv) using the presence or degree of such binding as a measure of the presence of a nucleosome-protein adduct in the sample.

According to another aspect of the invention there is provided a method for detecting and measuring cell free nucleosome adducts in a sample by an immunometric immunoassay which comprises the steps of:
  (i) contacting a sample which may contain nucleosome adducts containing a particular protein with a first antibody or other binder which binds to the protein of interest;
  (ii) contacting the nucleosomes or sample with a second antibody or other binder which binds to nucleosomes or a component thereof;
  (iii) detecting and/or quantifying the binding of said second antibody or other binder to nucleosomes sample with a second antibody or other binder which binds to nucleosomes or a component thereof in the sample; and
  (iv) using the presence or degree of such binding as a measure of the presence of a nucleosome adduct in the sample.

It will be clear to those skilled in the art that the antibody or other binder used to bind nucleosomes or a component thereof in stage (i) of the first aspect above and stage (ii) of the second aspect above may be an antibody (or other binder) directed against intact nucleosomes or against any component part of a nucleosome including without limitation against a histone, a histone variant, a histone modification, a nucleotide, a modified nucleotide or other part of the DNA component of a nucleosome. Thus in a further aspect of the invention there is provided a method for detecting (only) those nucleosome-protein adducts which additionally contain another feature to which this binder is directed including without limitation a particular histone modification, histone variant or nucleotide. An advantage of this design is that the nucleosome component epitope and adducted protein epitope of the assay can be selected to be epitopes whose levels both differ greatly in healthy or diseased patients, or other patient status under investigation. Thus is likely to reduce the proportion of nucleosomes detected by the assay but to increase the clinical selectivity or specificity of the assay.

We have performed this design of assay using an antibody directed to the nucleosome component H2AZ as the anti-nucleosome antibody in conjunction with anti-EZH2 antibodies and shown that nucleosome-EZH2 adducts specifically associated with H2AZ can be detected by such assays and that these assays can be used to discriminate between samples taken from healthy and diseased subjects.

In a further aspect of the invention the nucleosome adduct to be detected may contain more than one protein. Further proteins in an adduct may be directly or indirectly bound to the nucleosome. For example a nucleosome may be bound to a HMGB protein and additionally to a further protein or proteins. The further protein(s) may be directly bound to the nucleosome or may be bound to the HMGB protein, and hence indirectly to the nucleosome. Nucleosome adducts may contain large protein complexes consisting of multiple protein components where the binding of a particular protein in the complex adduct to the nucleosome may be through multiple intermediary binding connections. It will be clear to those skilled in the art that a protein bound to a nucleosome in a nucleosome adduct, either directly or indirectly, may be detected by a method of the present invention.

It will be clear to those skilled in the art that the methods of the invention described include a variety of embodiments including biosensor type assays and label-free assays of the type marketed for example by ForteBio Incorporated of USA.

According to a further aspect of the invention there is provided a method for detecting the proportion of nucleosomes that comprises a particular nucleosome adduct in a sample comprising the steps of:
  (i) detecting or measuring the level of nucleosomes in a sample;
  (ii) detecting or measuring the level of a nucleosome adduct according to a method of the current invention; and
  (iii) using the two measurements to determine the proportion of nucleosomes that comprises the nucleotide adduct.

We have shown that the detection and measurement of nucleosome adducts in the blood taken from subjects can be used as a diagnostic method to identify subjects with cancer and to differentiate them from healthy subjects. According to a further aspect of the invention there is provided a method for detecting or diagnosing the presence of a disease by measuring or detecting the presence and/or the level or concentration of cell free nucleosome adducts in a body fluid, and using the detected level as a biomarker of the disease status of a subject including, without limitation, a clinical diagnosis of a disease, a differential diagnosis of disease type or subtype, or a disease prognosis, or a disease relapse, or a diagnosis of subject susceptibility to treatment regimens. It will be appreciated by those skilled in the art that body fluids used for diagnostic testing include without limitation blood, serum, plasma, urine, cerebrospinal fluid and other fluids. In a preferred embodiment the body fluid selected as the sample is blood, serum or plasma. The assay response, level, concentration or quantity of a nucleosome adduct in a body fluid may be expressed in absolute terms or relative terms, for example without limitation as a proportion of the total nucleosome level present or as a ratio to the level of nucleosomes containing another nucleosome structure such as a histone modification or to the level of total DNA.

In one embodiment of the invention the nucleosome adduct measurement is used as a member of a diagnostic panel of tests or measurements for the detection or diagnosis of the disease status of a subject including, without limitation, a clinical diagnosis of a disease, a differential diagnosis of disease type or subtype, or a disease prognosis, or a disease relapse, or a diagnosis of subject susceptibility to treatment regimens According to another aspect of the invention there is provided a method for detecting or measuring the presence and/or the level of chromatin binding of a protein in a cell which comprises the steps of:
(i) isolating chromatin from a cell;
(ii) breaking down the chromatin to form mono-nucleosomes and/or oligo-nucleosomes; and
(iii) detecting or measuring the presence of a nucleosome adduct in the mono-nucleosomes and/or oligo-nucleosomes by means of an immunoassay method of the invention.

Methods for producing mono-nucleosomes and/or oligo-nucleosomes from chromatin are well known in the art and include enzyme digestion and sonication (Dai et al, 2011). We have demonstrated this aspect for nucleosomes produced from Hela and from MCF7 cells.

It will be clear to those skilled in the art that the terms antibody, binder or ligand in regard to any aspect of the invention is not limiting but intended to include antibody fragments, aptamers or any binder capable of binding to particular molecules or entities and that any suitable binder can be used in the method of the invention. It will also be clear that the term nucleosomes is intended to include mononucleosomes and oligonucleosomes and any such chromatin fragments that can be analysed in fluid media.

According to another aspect of the invention there is provided a kit for detecting or measuring nucleosome adducts which comprises a ligand or binder specific for the nucleosome adduct or a component part thereof, or a structural/shape mimic of the nucleosome adduct or component part thereof, together with instructions for use of the kit in accordance with any of the methods defined herein.

According to another aspect of the invention there is provided a method for identifying a nucleosome adduct biomarker for detecting or diagnosing disease status in animals or humans which comprises the steps of:
(i) detecting or measuring the level of a cell free nucleosome adduct in a body fluid of diseased subjects;
(ii) detecting or measuring the level of a cell free nucleosome adduct in a body fluid of control subjects; and
(iii) using the difference between the levels detected in diseased and control subjects to identify whether a nucleosome adduct is useful as a biomarker for that disease.

It will be clear to those skilled in the art that the control subjects may be selected on a variety of basis which may include, for example, subjects known to be free of the disease or may be subjects with a different disease (for example; for the investigation of differential diagnosis).

According to a further aspect of the invention there is provided a method for identifying a nucleosome adduct biomarker for assessing the prognosis of a diseased animal or human subject which comprises the steps of:
(i) detecting or measuring the level of a cell free nucleosome adduct in a body fluid of diseased subjects; and
(ii) correlating the level of cell free nucleosome adduct detected in a body fluid of diseased subjects with the disease outcome of the subjects.

According to a further aspect of the invention there is provided a method for identifying a nucleosome adduct biomarker to be used for the selection of a treatment regimen for a diseased animal or human subject in need of treatment which comprises the steps of:
(i) detecting or measuring the level of a cell free nucleosome adduct in a body fluid of diseased subjects; and
(ii) correlating the level of cell free nucleosome adduct detected in a body fluid of diseased subjects with the observed efficacy of a treatment regimen in those subjects.

According to a further aspect of the invention there is provided a method for identifying a nucleosome adduct biomarker to be used for monitoring the treatment of a diseased animal or human subject which comprises the steps of:
(i) detecting or measuring the level of a cell free nucleosome adduct in a body fluid of a diseased subject;
(ii) repeating said detection or measurement on one or more occasions during the disease progression of the subject; and
(iii) correlating the level of cell free nucleosome adduct detected in a body fluid of a diseased subject with the disease progression in the subject.

According to a further aspect of the invention, there is provided a biomarker identified by the method as defined herein.

A further aspect of the invention provides ligands or binders, such as naturally occurring or chemically synthesised compounds, capable of specific binding to the biomarker. A ligand or binder according to the invention may comprise a peptide, an antibody or a fragment thereof, or a synthetic ligand such as a plastic antibody, or an aptamer or oligonucleotide, capable of specific binding to the biomarker. The antibody can be a monoclonal antibody or a fragment thereof capable of specific binding to the biomarker. A ligand according to the invention may be labeled with a detectable marker, such as a luminescent, fluorescent, enzyme or radioactive marker; alternatively or additionally a ligand according to the invention may be labelled with an affinity tag, e.g. a biotin, avidin, streptavidin or His (e.g. hexa-His) tag. Alternatively ligand binding may be determined using a label-free technology for example that of ForteBio Inc.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the biomarker. In these uses, the detection and/or quantification can be performed on a biological sample as defined herein.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit for detecting the presence of a disease state, comprising a biosensor capable of detecting and/or quantifying one or more of the biomarkers as defined herein.

Biomarkers for detecting the presence of a disease are essential targets for discovery of novel targets and drug molecules that retard or halt progression of the disorder. As the level of the biomarker is indicative of disorder and of drug response, the biomarker is useful for identification of novel therapeutic compounds in in vitro and/or in vivo assays. Biomarkers of the invention can be employed in methods for screening for compounds that modulate the activity of the biomarker.

Thus, in a further aspect of the invention, there is provided the use of a binder or ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying subjects most likely to respond to a particular therapeutic treatment, drug screening and development. Biomarkers and uses thereof are valuable for identification of new drug treatments and for discovery of new targets for drug treatment.

The terms "detecting" and "diagnosing" as used herein encompass identification, confirmation, and/or characterisation of a disease state. Methods of detecting, monitoring and of diagnosis according to the invention are useful to confirm the existence of a disease, to monitor development of the disease by assessing onset and progression, or to assess amelioration or regression of the disease. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "subject solutions" with the potential for improved prognosis, by establishing the correct diagnosis, allowing rapid identification of the most appropriate treatment (thus lessening unnecessary exposure to harmful drug side effects), and reducing relapse rates.

In one embodiment, said biomarker is released from the cells of a tumour. Thus, according to a further aspect of the invention there is provided a method for the detection of a tumour growth which comprises the steps of (i) measuring a biomarker in a biological sample that is associated with or released from the cells of a tumour and (ii) demonstrating that the level of said biomarker is associated with the size, stage, aggressiveness or dissemination of the tumour.

It is known that increased cell turnover, cell death and apoptosis lead to increased circulatory levels of cell free nucleosomes (Holdenrieder et al, 2001). Circulating cell free nucleosomes level is a non-specific indicator and occurs in a variety of conditions including inflammatory diseases, a large variety of benign and malignant conditions, autoimmune diseases; as well as following trauma or ischaemia (Holdenrieder et al 2001). It will be clear to those skilled in the art that the invention will have application in a variety of disease areas where circulating nucleosomes have been found in subjects. These include, without limitation, trauma (for example; severe injury or surgery), extreme exercise (for example running a marathon), stroke and heart attack, sepsis or other serious infection and endometriosis.

The immunoassays of the invention include immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays and competitive immunoassay methods including labelled antigen and labelled antibody competitive immunoassay methods with a variety of label types including radioactive, enzyme, fluorescent, time-resolved fluorescent and particulate labels. All of said immunoassay methods are well known in the art, see for example Salgame et al, 1997 and van Nieuwenhuijze et al, 2003.

In one embodiment, said biological sample comprises a body fluid. For example, biological samples that may be tested in a method of the invention include cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include specimens from a live subject, or taken post-mortem. The samples can be prepared, for example where appropriate diluted or concentrated, and stored in the usual manner.

In one embodiment, the method of the invention is repeated on multiple occasions. This embodiment provides the advantage of allowing the detection results to be monitored over a time period. Such an arrangement will provide the benefit of monitoring or assessing the efficacy of treatment of a disease state. Such monitoring methods of the invention can be used to monitor onset, progression, stabilisation, amelioration, relapse and/or remission.

Thus, the invention also provides a method of monitoring efficacy of a therapy for a disease state in a subject, suspected of having such a disease, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The Method may comprise detecting a change in the nature or amount of the biomarker(s) in test samples taken on different occasions.

Thus, according to a further aspect of the invention, there is provided a method for monitoring efficacy of therapy for a disease state in a human or animal subject, comprising:
(a) quantifying the amount of the biomarker as defined herein; and
(b) comparing the amount of said biomarker in a test sample with the amount present in one or more control(s) and/or one or more previous test sample(s) taken at an earlier time from the same test subject.

A change in the level of the biomarker in the test sample relative to the level in a previous test sample taken earlier from the same test subject may be indicative of a beneficial effect, e.g. stabilisation or improvement, of said therapy on the disorder or suspected disorder. Furthermore, once treatment has been completed, the method of the invention may be periodically repeated in order to monitor for the recurrence of a disease.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

In a further embodiment the monitoring of more rapid changes due to fast acting therapies may be conducted at shorter intervals of hours or days.

According to a further aspect of the invention, there is provided a method for identifying a biomarker for detecting the presence of a disease state. The term "identifying" as used herein means confirming the presence of the biomarker present in the biological sample. Quantifying the amount of the biomarker present in a sample may include determining the concentration of the biomarker present in the sample. Identifying and/or quantifying may be performed directly on the sample, or indirectly on an extract therefrom, or on a dilution thereof.

In alternative aspects of the invention, the presence of the biomarker is assessed by detecting and/or quantifying antibody or fragments thereof capable of specific binding to the biomarker that are generated by the subject's body in response to the biomarker and thus are present in a biological sample from a subject having a disease state.

Identifying and/or quantifying can be performed by any method suitable to identify the presence and/or amount of a specific protein in a biological sample from a subject or a purification or extract of a biological sample or a dilution thereof. In methods of the invention, quantifying may be performed by measuring the concentration of the biomarker in the sample or samples. Biological samples that may be tested in a method of the invention include those as defined hereinbefore. The samples can be prepared, for example where appropriate diluted or concentrated, and stored in the usual manner.

Identification and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. It is noted in particular that peptides of the same or related sequence to that of histone tails are particularly useful fragments of histone proteins.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand or binder may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate. LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample by SELDI TOF or MALDI TOF to detect the presence or level of the biomarker. These methods are also suitable for clinical screening, prognosis, monitoring the results of therapy, identifying subjects most likely to respond to a particular therapeutic treatment, for drug screening and development, and identification of new targets for drug treatment.

Identifying and/or quantifying the analyte biomarkers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

In one embodiment, one or more of the biomarkers may be replaced by a molecule, or a measurable fragment of the molecule, found upstream or downstream of the biomarker in a biological pathway.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, identifying and quantifying can be performed using a biosensor, microanalytical system, microengineered system, microseparation system, immunochromatography system or other suitable analytical devices. The biosensor may incorporate, an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

As used herein, the term "biosensor" means anything capable of detecting the presence of the biomarker. Examples of biosensors are described herein.

Biosensors according to the invention may comprise a ligand binder or ligands, as described herein, capable of specific binding to the biomarker. Such biosensors are useful in detecting and/or quantifying a biomarker of the invention.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g. in the ward, outsubjects' department, surgery, home, field and workplace.

Biosensors to detect one or more biomarkers of the invention include acoustic, plasmon resonance, holographic, Bio-Layer Interferometry (BLI) and microengineered sensors. Imprinted recognition elements, thin film transistor technology, magnetic acoustic resonator devices and other novel acousto-electrical systems may be employed in biosensors for detection of the one or more biomarkers of the invention.

Methods involving identification and/or quantification of one or more biomarkers of the invention can be performed on bench-top instruments, or can be incorporated onto disposable, diagnostic or monitoring platforms that can be used in a non-laboratory environment, e.g. in the physician's office or at the subject's bedside. Suitable biosensors for performing methods of the invention include "credit" cards with optical or acoustic readers. Biosensors can be configured to allow the data collected to be electronically transmitted to the physician for interpretation and thus can form the basis for e-medicine.

Diagnostic kits for the diagnosis and monitoring of the presence of a disease state are described herein. In one embodiment, the kits additionally contain a biosensor capable of identifying and/or quantifying a biomarker. Suitably a kit according to the invention may contain one or more components selected from the group: a ligand binder, or ligands, specific for the biomarker or a structural/shape mimic of the biomarker, one or more controls, one or more reagents and one or more consumables; optionally together with instructions for use of the kit in accordance with any of the methods defined herein.

The identification of biomarkers for a disease state permits integration of diagnostic procedures and therapeutic regimes. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions.

Thus by monitoring a biomarker of the invention, subject care can be tailored precisely to match the needs determined by the disorder and the pharmacogenomic profile of the subject, the biomarker can thus be used to titrate the optimal dose, predict a positive therapeutic response and identify those subjects at high risk of severe side effects.

Biomarker-based tests provide a first line assessment of 'new' subjects, and provide objective measures for accurate and rapid diagnosis, not achievable using the current measures.

Furthermore, diagnostic biomarker tests are useful to identify family members or subjects with mild or asymptomatic disease or who may be at high risk of developing symptomatic disease. This permits initiation of appropriate therapy, or preventive measures, e.g. managing risk factors. These approaches are recognised to improve outcome and may prevent overt onset of the disorder.

Biomarker monitoring methods, biosensors and kits are also vital as subject monitoring tools, to enable the physician to determine whether relapse is due to worsening of the disorder. If pharmacological treatment is assessed to be inadequate, then therapy can be reinstated or increased; a change in therapy can be given if appropriate. As the biomarkers are sensitive to the state of the disorder, they provide an indication of the impact of drug therapy.

The invention will now be illustrated with reference to the following non-limiting examples.

EXAMPLE 1

Serum samples were taken from 5 healthy subjects, 3 subjects with colon cancer, 6 subjects with lung cancer and 2 subjects with pancreatic cancer. A commercially available nucleosome preparation produced by digestion of chromatin extracted from Hela cells, in which the DNA and proteins in the nucleosome are cross-linked for stability, was serially diluted in horse serum. A nucleosome preparation in human blood was prepared according to the method of Holdenrieder (*Holdenrieder et al; 2001). These samples and preparations were assayed in duplicate for nucleosome-EZH2 adduct by the method of the invention. Neat commercially available horse serum produced for use in tissue culture was also assayed as a negative control sample containing no nucleosomes or nucleosome adducts.

Figure 2:
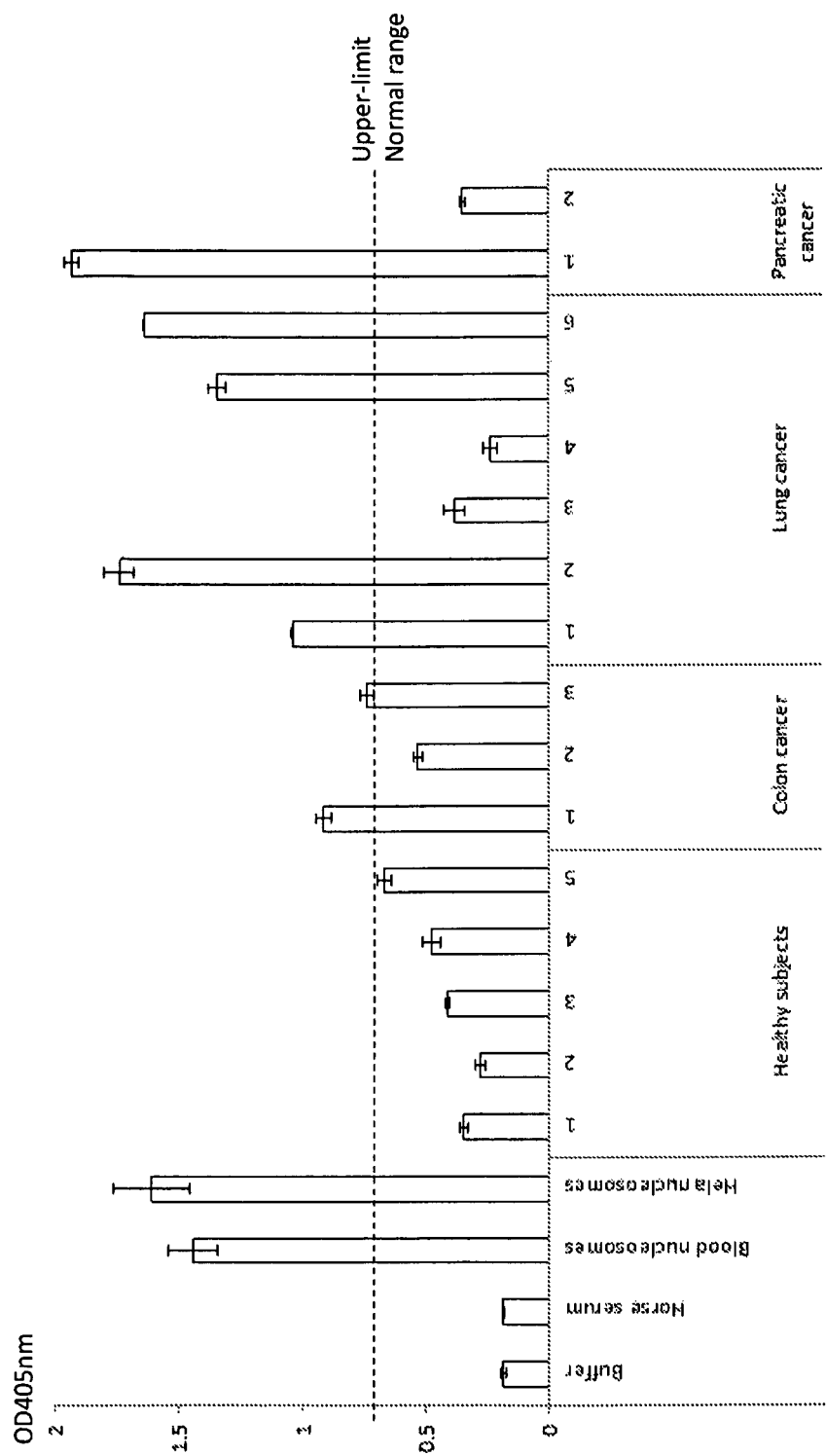
FIG. 2: Nucleosome-EZH2 adduct ELISA results for serum samples taken from 5 healthy subjects and 11 subjects with tumours.

The ELISA method used a solid phase anti-histone capture antibody that binds intact nucleosomes and a biotinylated monoclonal anti-EZH2 detection antibody as follows: A solution of anti-histone antibody in 0.1M phosphate buffer pH 7.4 was added to microtitre wells (100 µL/well) and incubated overnight at 4° C. to coat the wells with capture antibody. Excess anti-histone antibody was decanted. A solution of bovine serum albumin (20 g/L) was added to the wells (200 µL/well) and incubated for 30 minutes at room temperature to block excess protein binding sites on the wells. Excess bovine serum albumin solution was decanted and the wells were washed three times with wash buffer (200 µL/well, 0.05M TRIS/HCl buffer pH 7.5 containing 1% Tween 20). Serum sample (10 µL/well) and assay buffer (50 µL/well, 0.05M TRIS/HCl pH 7.5 containing 0.9% NaCl, 0.05% sodium deoxycholate and 1% Nonidet P40 substitute) were added to the wells incubated overnight at 4° C. The serum and assay buffer mixture was decanted and the wells were washed three times with wash buffer (200 µL/well). A solution of biotinylated anti-EZH2 detection antibody was added (50 µL/well) and incubated for 90 minutes at room temperature with mild agitation. Excess detection antibody was decanted and the wells were again washed three times with wash buffer (200

μL/well). A solution containing a streptavidin-horse radish peroxidase conjugate was added (50 μL/well) and incubated for 30 minutes at room temperature with mild agitation. Excess conjugate was decanted and the wells were again washed three times with wash buffer (200 μL/well). A coloured substrate solution (100 μL/well, 2,2'-Azinobis [3-ethylbenzothiazoline-6-sulfonic acid]-diammonium salt) was added and incubated for 20 minutes at room temperature with mild agitation. The optical density (OD) of the wells was measured at a wavelength of 405 nm using a standard microtitre plate reader. A dose response curve of increasing colour with increasing nucleosome-EZH2 adduct concentration was observed with a low background signal observed in the absence of nucleosome adduct (horse serum). The positive ELISA signal indicates that the EZH2 detected by the ELISA is incorporated within a nucleosome-EZH2 adduct comprising both histone protein and EZH2 as (i) the capture antibody binds to histones in the sample and (ii) detection antibody binds to the EZH2 component of the adduct. The results are shown in FIGS. 1 and 2.

EXAMPLE 2

Serum samples were taken from 5 healthy subjects, 3 subjects with colon cancer, 6 subjects with lung cancer and 2 subjects with pancreatic cancer. A commercially available nucleosome preparation produced by digestion of chromatin extracted from Hela cells, was serially diluted in horse serum. A nucleosome preparation in human blood was prepared according to the method of Holdenrieder (*Holdenrieder of al; 2001). These samples and preparations were assayed in duplicate for nucleosome-HMGB1 adduct by the method of the invention. Neat horse serum was also assayed as a negative control sample containing no nucleosomes or nucleosome adducts.

Figure 3:
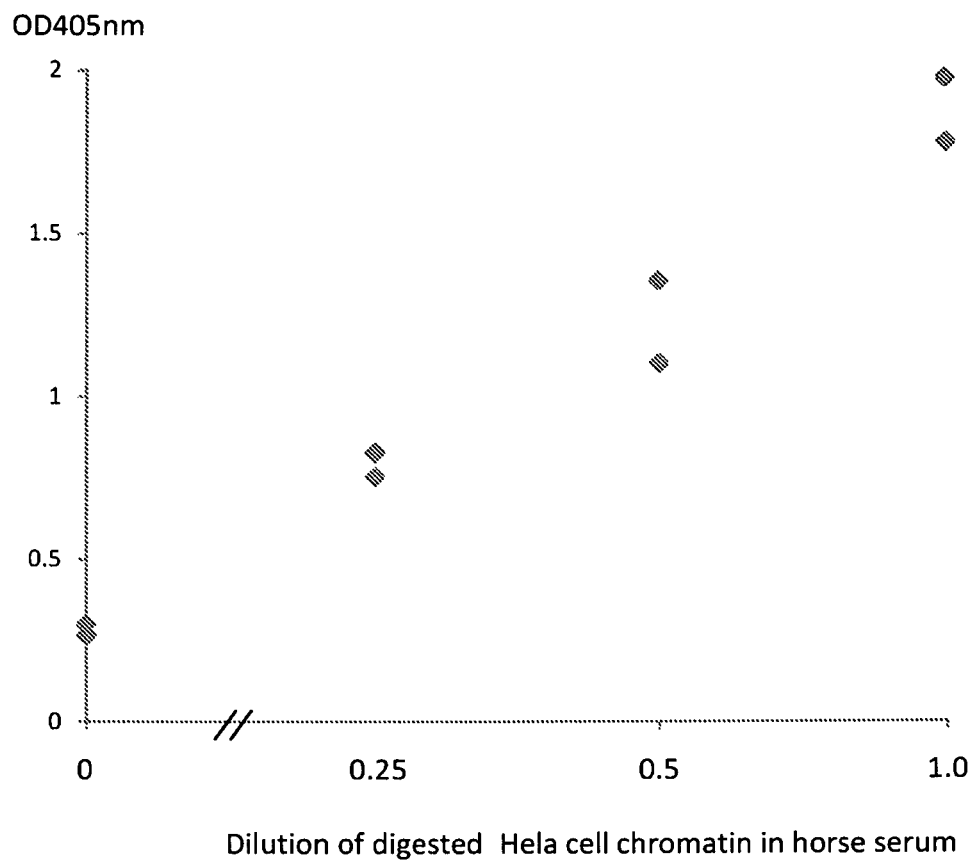
FIG. 3: ELISA dose response curve for the detection of nucleosome-HMGB1 adduct levels in digested chromatin extracted from Hela cells diluted into horse serum.
Figure 4:
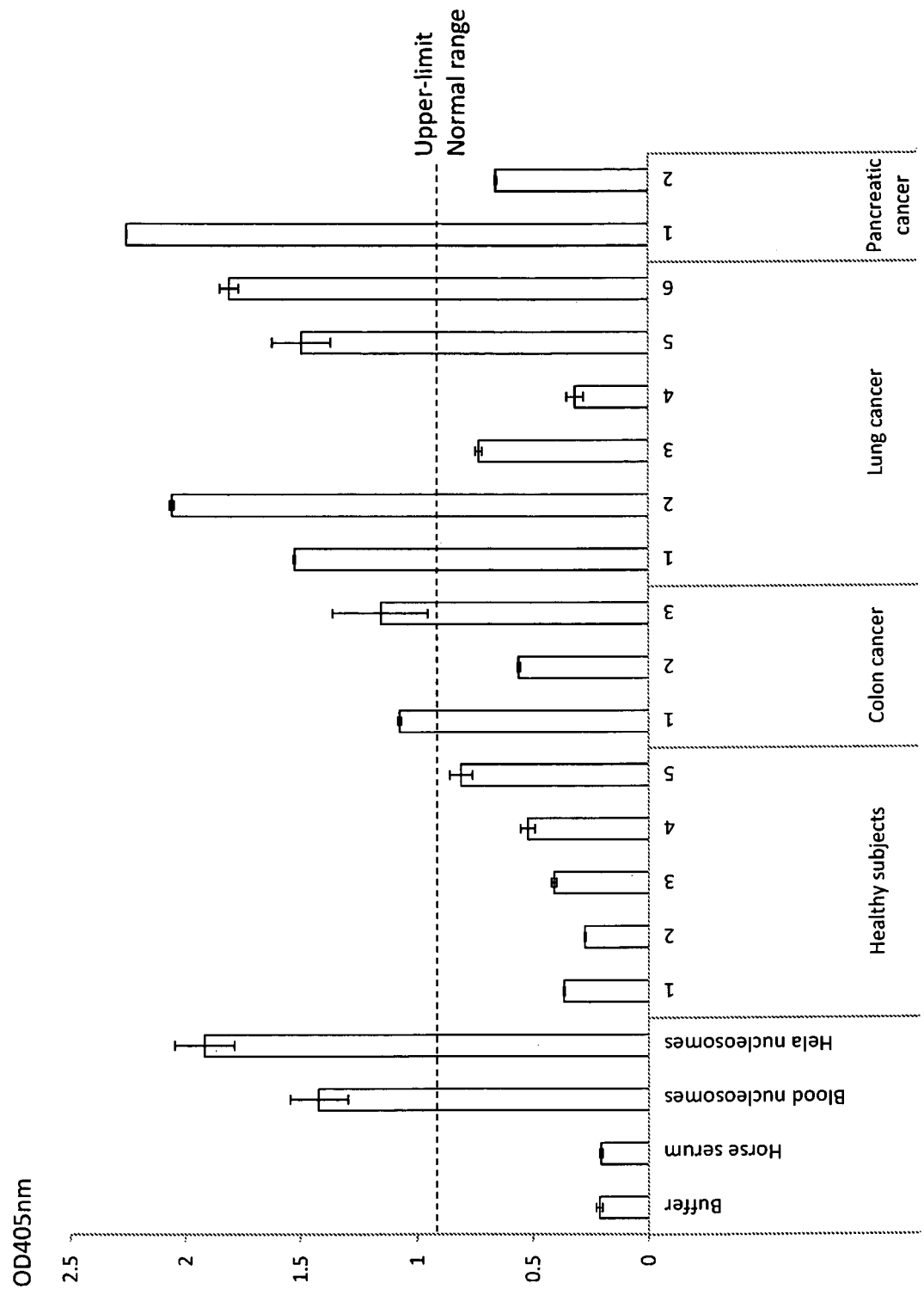
FIG. 4: Nucleosome-HMGB1 adduct ELISA results for serum samples taken from 5 healthy subjects and 11 subjects with tumours.

The ELISA method used a solid phase anti-histone capture antibody that binds intact nucleosomes and a biotinylated monoclonal anti-HMGB1 detection antibody as follows: A solution of anti-histone antibody in 0.1M phosphate buffer pH 7.4 was added to microtitre wells (100 μL/well) and incubated overnight at 4° C. to coat the wells with capture antibody. Excess anti-histone antibody was decanted. A solution of bovine serum albumin (20 g/L) was added to the wells (200 μL/well) and incubated for 30 minutes at room temperature to block excess protein binding sites on the wells. Excess bovine serum albumin solution was decanted and the wells were washed three times with wash buffer (200 μL/well, 0.05M TRIS/HCl buffer pH 7.5 containing 1% Tween 20). Serum sample (10 μL/well) and assay buffer (50 μL/well, 0.05M TRIS/HCl pH 7.5 containing 0.9% NaCl, 0.05% sodium deoxycholate and 1% Nonidet P40 substitute) were added to the wells incubated overnight at 4° C. The serum and assay buffer mixture was decanted and the wells were washed three times with wash buffer (200 μL/well). A solution of biotinylated anti-HMGB1 detection antibody was added (50 μL/well) and incubated for 90 minutes at room temperature with mild agitation. Excess detection antibody was decanted and the wells were again washed three times with wash buffer (200 μL/well). A solution containing a streptavidin-horse radish peroxidase conjugate was added (50 μL/well) and incubated for 30 minutes at room temperature with mild agitation. Excess conjugate was decanted and the wells were again washed three times with wash buffer (200 μL/well). A coloured substrate solution (100 μL/well, 2,2'-Azinobis [3-ethylbenzothiazoline-6-sulfonic acid]-diammonium salt) was added and incubated for 20 minutes at room temperature with mild agitation. The optical density (OD) of the wells was measured at a wavelength of 405 nm using a standard microtitre plate reader. A dose response curve of increasing colour with increasing nucleosome-HMGB1 adduct concentration was observed with a low background signal observed in the absence of nucleosome adduct (horse serum). The positive ELISA signal indicates that the HMGB1 detected by the ELISA is incorporated in a nucleosome-HMGB1 adduct comprising both histone protein and HMGB1 as (i) the capture antibody binds to histones in the sample and (ii) detection antibody binds to the HMGB1 component of the adduct. The results are shown in FIGS. 3 and 4.

Figure 5:
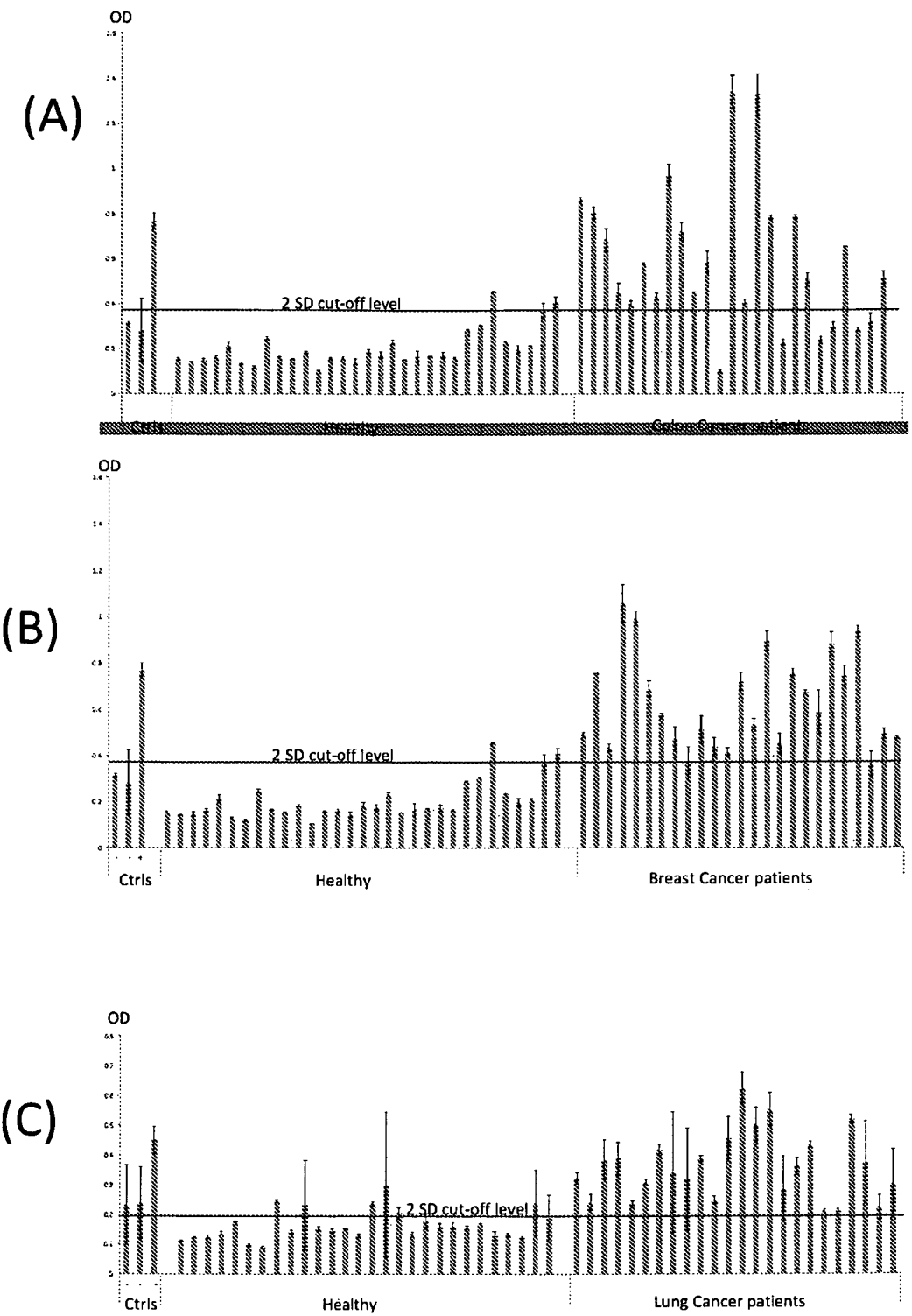
FIG. 5: Nucleosome-HMGB1 adduct ELISA results for serum samples taken from 31 healthy subjects and 74 subjects with (A) colon cancer, (B) breast cancer or (C) lung cancer.

In a larger experiment, serum samples were taken from 25 patients with colon cancer, 25 patients with breast cancer and 24 patients with lung cancer as well as samples from 31 healthy subjects. The samples were tested for nucleosome-HMGB1 level and, using the mean healthy result plus 2 standard deviations in the mean as cut-off, the following results were obtained for colon, breast and lung cancer:

Colon: 76% of cancers were detected (19 of 25 patients) and 90% specificity (3 false positives from 31 healthy samples);

Breast: 96% of cancers were detected (24 of 25 patients) and 90% specificity (3 false positives from 31 healthy samples); and Lung: 100% of cancers were detected (24 of 24 patients) and 86% specificity (4 false positives from 28 healthy samples);

where a measured nucleosome-HMGB1 adduct level above the cut-off level is considered a positive result and a lower level is considered a negative result. The results are shown in FIG. 5.

The assay for nucleosome-HMGB1 adduct levels was also carried out in the reverse format where the anti-HMGB1 antibody was coated to wells as capture antibody and the anti-nucleosome antibody was biotinylated and used as detection antibody. This format of the assay also successfully detected nucleosome-HMGB1 adducts in the positive controls used (OD405 nm=1.15) but not in either horse serum or buffer (both OD406 nm=0.13)

EXAMPLE 3

Figure 6:
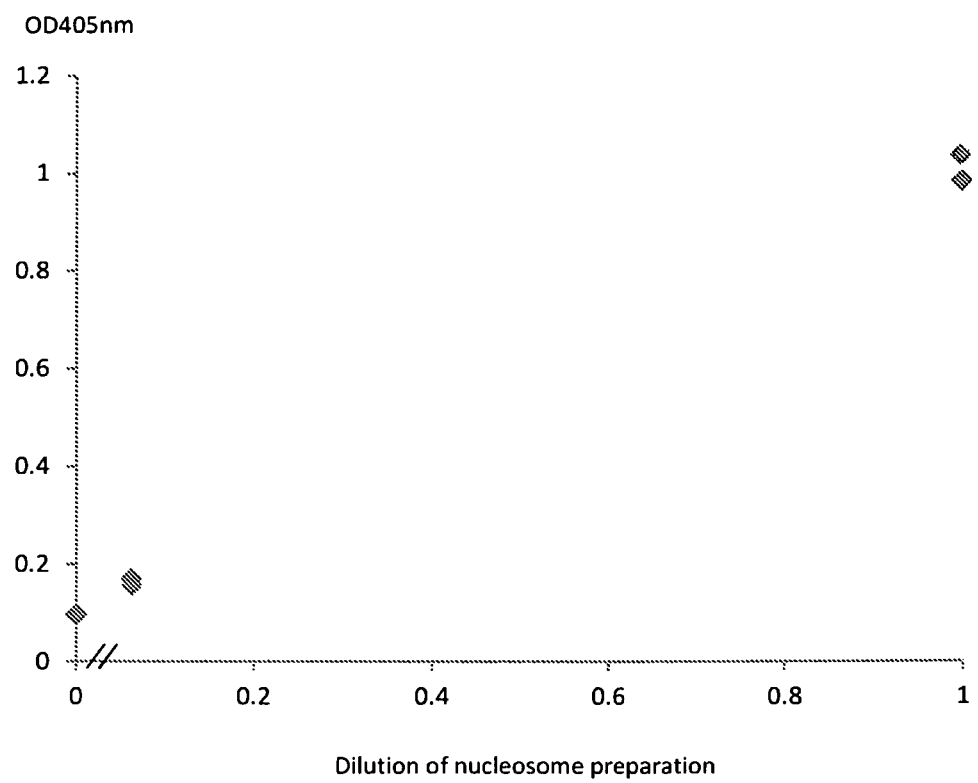
FIG. 6: ELISA dose response curve for the detection of nucleosome-Progesterone Receptor adduct levels in cell-free nucleosomes prepared by the method of *Holdenrieder et al; 2001.

A nucleosome-PR ELISA assay was carried out using the method of Example 1 above except that the biotinylated antibody used was directed to bind the progesterone receptor (PR). The results are shown in FIG. 6.

EXAMPLE 4

Figure 7:
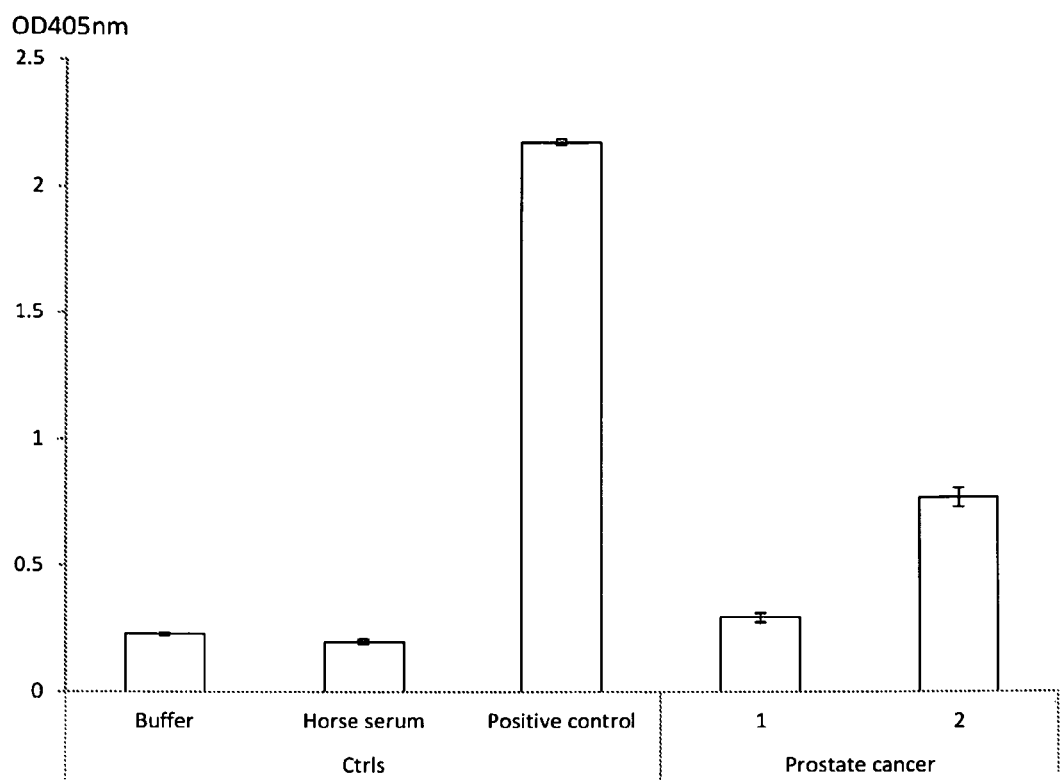
FIG. 7: ELISA results for the detection of nucleosome-Androgen Receptor adduct levels in 2 prostate cancer cases and a cell-free nucleosome sample prepared by the method of *Holdenrieder et al; 2001.

Serum samples taken from two prostate cancer patients, as well as positive and negative controls, were assayed using a nucleosome-AR adduct ELISA assay carried out using the method of Example 1 above except that the biotinylated antibody used was directed to bind the androgen receptor (AR). The results are shown in FIG. 7.

EXAMPLE 5

Figure 8:
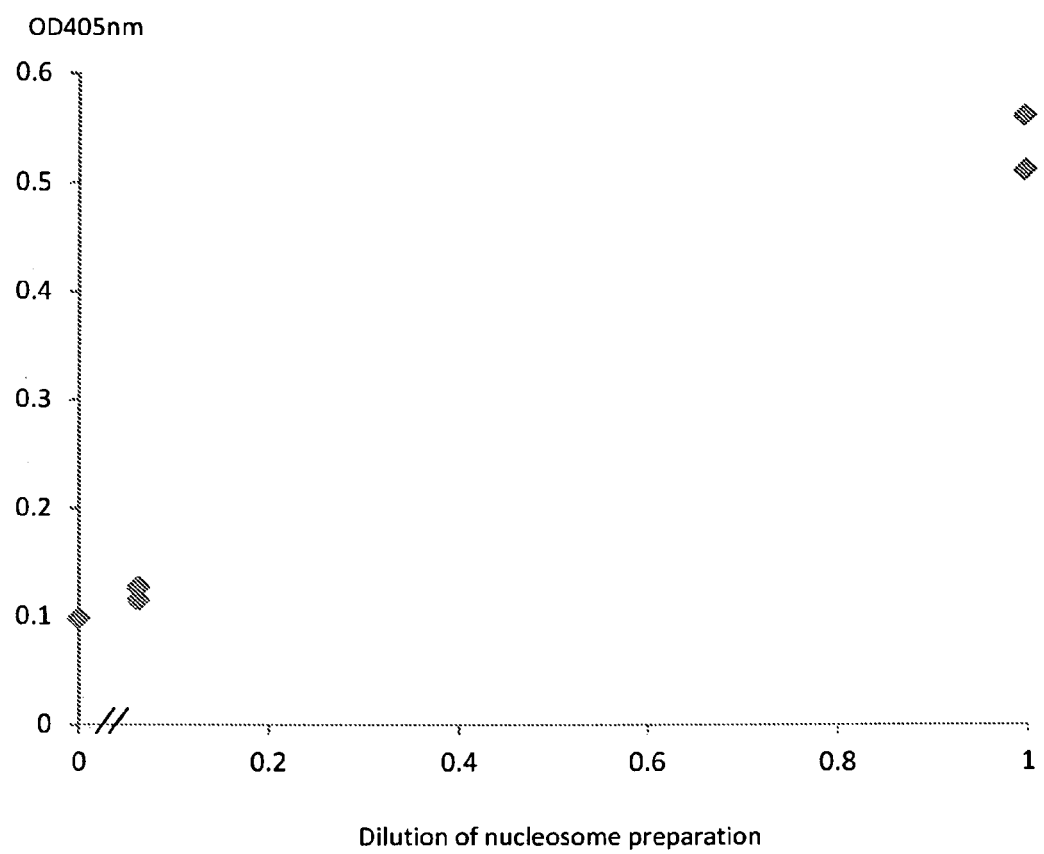
FIG. 8: ELISA dose response curve for the detection of nucleosome-Estrogen Receptor alpha (ERα) adduct levels in cell-free nucleosomes prepared by the method of *Holdenrieder et al; 2001.

A nucleosome-ERα adduct ELISA assay was carried out using a nucleosome sample prepared by the method of *Holdenrieder et al; 2001 by the method of Example 1 above except that the biotinylated antibody used was directed to bind the alpha form of the estrogen receptor (ERα). The results are shown in FIG. 8.

EXAMPLE 6

Figure 9:
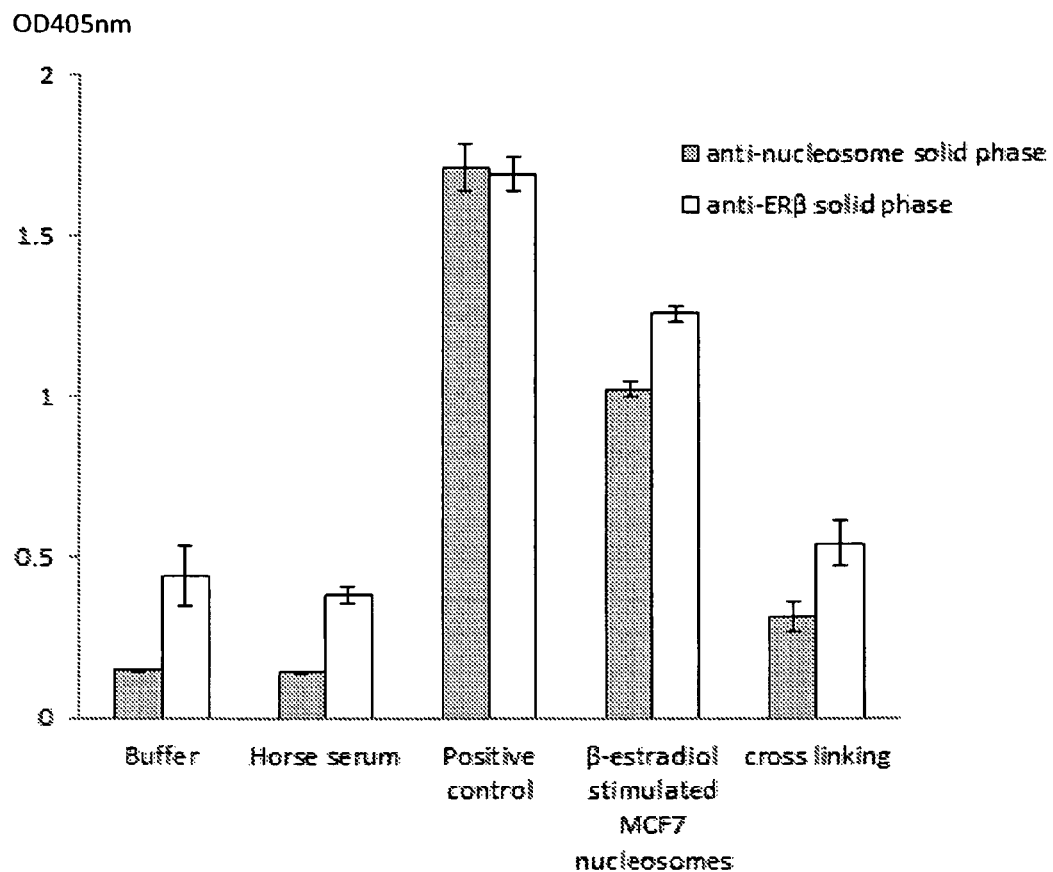
FIG. 9: ELISA results for the detection of nucleosome-ERβ adduct levels in digested MCF7 chromatin. The assay was carried out in two different formats. In the first format the anti-nucleosome antibody was coated on the wells and the anti-ERβ antibody was biotinylated. In the second format the anti-ERβ antibody was coated on the wells and the anti-nucleosome antibody was biotinylated.

A nucleosome sample was prepared by digestion of chromatin extracted from MCF7 cells and assayed for nucleosome-ERβ adduct by ELISA. The assay was carried out by a method similar to that of Example 1 above except that the assay was performed using a different anti-nucleosome antibody and an antibody directed to bind the beta form of the estrogen receptor (ERβ). The assay was carried out in two different formats. In the first format the anti-nucleosome antibody was coated on the wells and the anti-ERβ antibody was biotinylated. In the second format the anti-ERβ antibody was coated on the wells and the anti-nucleosome antibody was biotinylated. The assay was successful in both formats. Interestingly the assay appeared to perform less well when the MCF7 chromatin was cross-linked as is often done in ChIP methods. The results are shown in FIG. 9.

EXAMPLE 7

Figure 10:
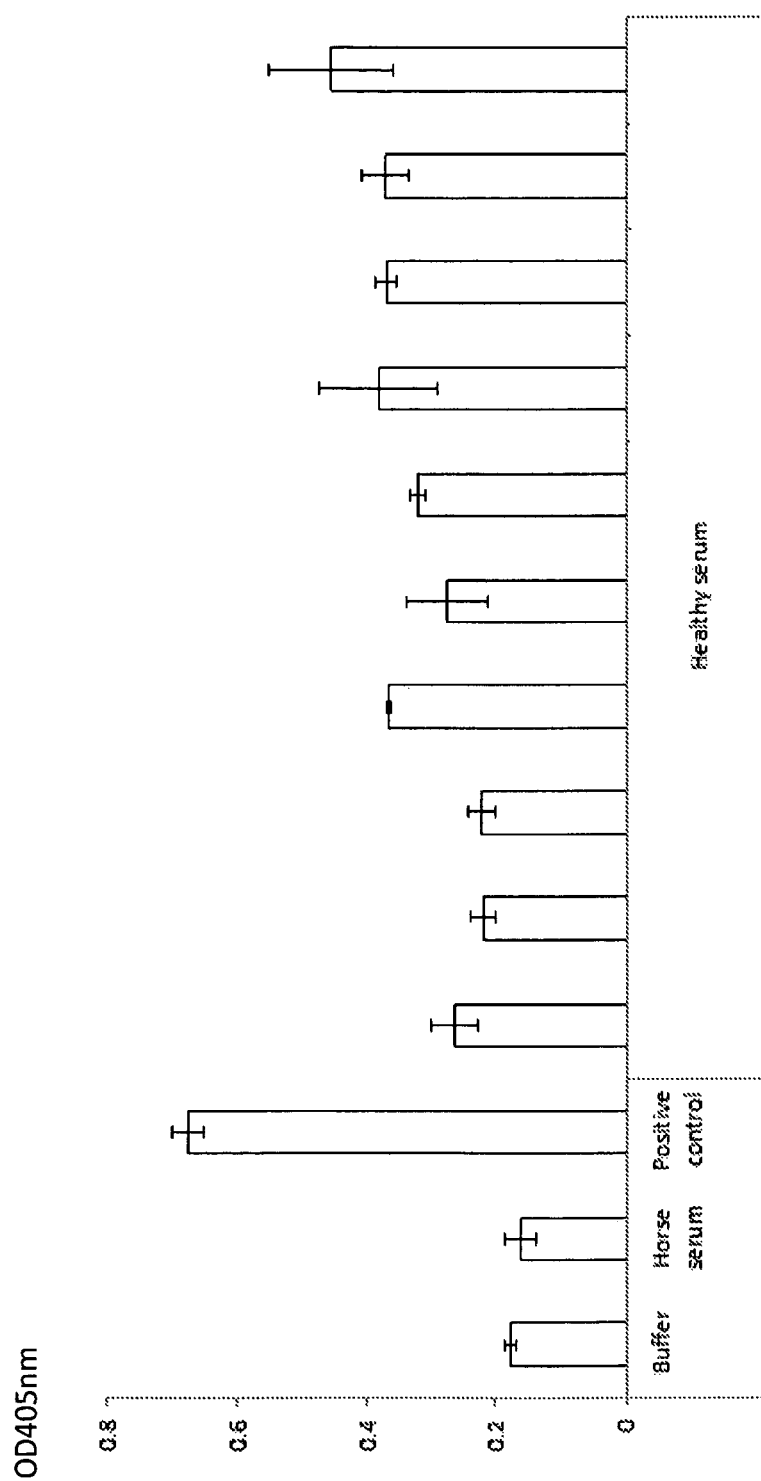
FIG. 10: Nucleosome H2AZ-ERβ adduct ELISA results.

A nucleosome H2AZ-ERβ adduct ELISA assay was carried out using a nucleosome sample prepared by the method of *Holdenrieder et al; 2001 by the method of Example 6 above where the anti-ERβ antibody was coated on the wells except that the biotinylated antibody used was directed to bind the histone variant H2AZ such that only the subset of nucleosome-ERβ adducts containing H2AZ were detected. Using this method, wherein the nucleosome or nucleosome component binder is directed to bind to a particular epigenetic signal structure, it is possible to detect a particular subset of nucleosome adducts containing only that epigenetic signal. The results are shown in FIG. 10.

EXAMPLE 8

Figure 11:
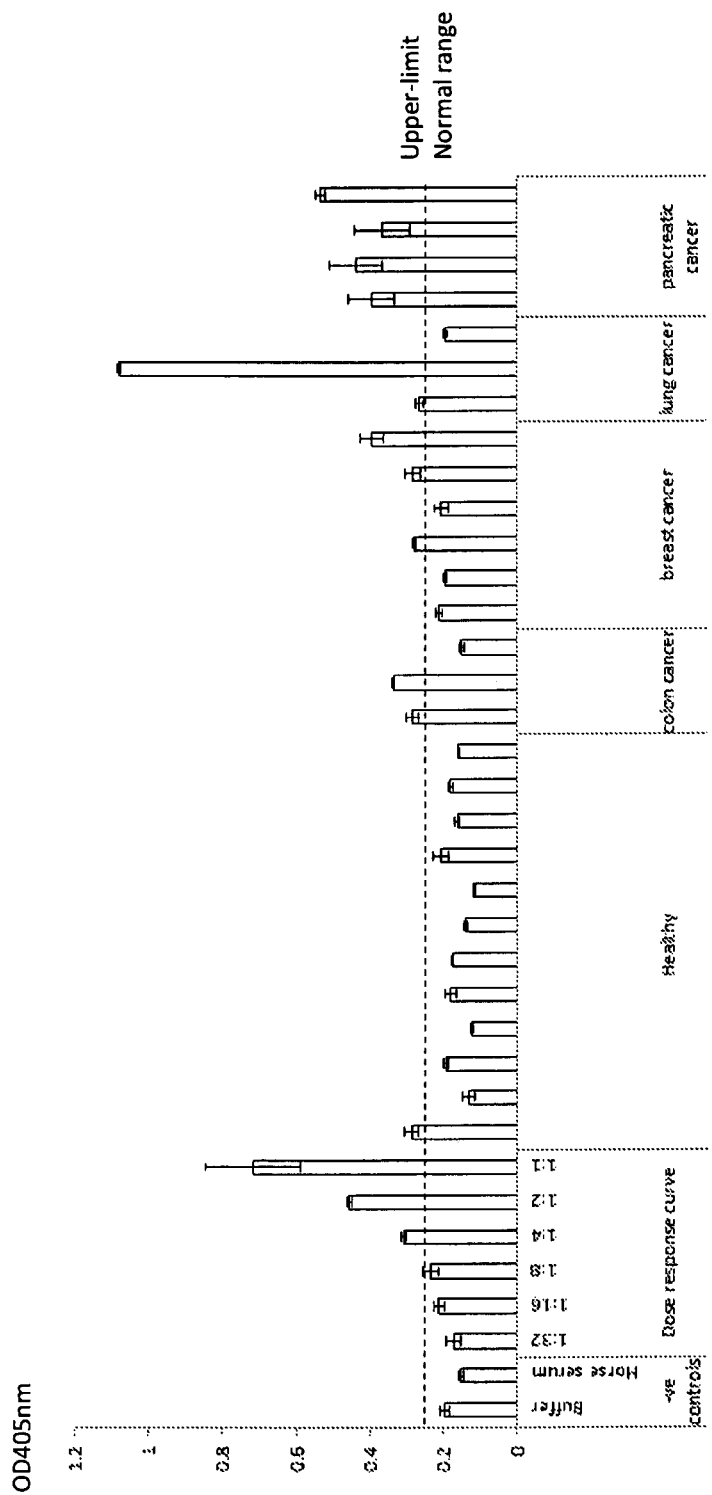
FIG. 11: Nucleosome-ERβ adduct ELISA results for serum samples taken from 12 healthy subjects and 16 subjects with tumours.

Serum samples were taken from 12 healthy subjects, 3 subjects with colon cancer, 6 subjects with breast cancer, 3 subjects with lung cancer and 4 subjects with pancreatic cancer. A nucleosome preparation in human blood was prepared according to the method of Holdenrieder (*Holdenrieder et al; 2001) and was serially diluted in horse serum. These samples and preparations were assayed in duplicate for nucleosome-ERβ adduct by the method of the invention. Neat commercially available horse serum produced for use in tissue culture was also assayed as a negative control sample containing no nucleosomes or nucleosome adducts. The assay was carried out using the method of Example 1 above except that the detection antibody used was directed against the estrogen receptor (ERβ). Using a cut-off calculated as the mean healthy result plus 2 standard deviations of the mean; 2 of 3 colon cancer samples, 3 of 6 breast cancer samples, 2 of 3 lung cancer samples and 4 of 4 pancreatic cancer samples were found positive for nucleosome-ERβ adduct. The results are shown in FIG. 11.

EXAMPLE 9

A nucleosome-estrogen receptor-steroid estrogen ELISA assay is carried out using the method of Example 6 above except that the detection antibody used was directed against steroid estrogen. This assay therefor detected only nucleosome-estrogen receptor adducts that additionally contained steroid hormone.

EXAMPLE 10

A nucleosome-estrogen receptor-estrogen adduct ELISA assay is carried out using a method similar to that of Example above except that the assay is performed in a microtitre plate or tube that is resistant to organic solvents and, following anti-nucleosome antibody capture of nucleosome-estrogen receptor adducts on the surface of the well, the liquid contents of the well are decanted and diethylether is added to dissolve any steroid present in the captured adduct. The ether is transferred, to another well or tube and dried. The dried extract is redissolved in assay buffer and the estrogen concentration is determined using a classical competitive immunoassay method for estrogen analysis. This assay therefore detects only nucleosome-estrogen receptor adducts that additionally contain estrogen.

EXAMPLE 11

A nucleosome-retinoic acid receptor-retinoic acid ELISA assay is carried out using the method of Example 10 above except that the steroid competitive immunoassay used was directed against retinoic acid. This assay therefor detects only nucleosome-retinoic acid receptor adducts that additionally contain steroid retinoic acid.

EXAMPLE 12

Nucleosome adduct assays similar to those described in Examples 1-10 are performed except that the solid phase coated antibody used was directed against 5-methylcytidine. These assays therefor detect only nucleosome-hormone receptor adducts and nucleosome-hormone receptor-hormone complex adducts which are additionally associated with methylated DNA.

References

Allen et al, A simple method for estimating global DNA methylation using bisulfite PCR of repetitive DNA elements. Nucleic Acids Research: 32(3) e38DOI: 10.1093/nar/gnh032, 2004

Bawden et al, Detection of histone modification in cell-free nucleosomes. WO 2005/019826, 2005

Cao et al, Role of Histone H3 Lysine 27 Methylation in Polycomb-Group Silencing SCIENCE 298, 1039-1043, 2002

Dai et al, Detection of Post-translational Modifications on Native Intact Nucleosomes by ELISA. http://www.jove.com/details.php?id=2593 doi: 10.3791/2593. J Vis Exp. 50 (2011).

Esteller, Cancer epigenomics: DNA methylomes and histone-modification maps Nature Reviews Genetics: 8, 286-298, 2007

Feinberg and Vogelstein, Hypomethylation distinguishes genes of some human cancers from their normal counterparts. Nature: 301, 89-92, 1983

Fullgrabe et al, Histone onco-modifications. Oncogene: 30, 3391-3403, 2011 Gerlitz et al, The dynamics of HMG protein-chromatin interactions in living cells. Biochem Cell Biol, 87, 127-137, 2009

Grutzmann at al, Sensitive Detection of Colorectal Cancer in Peripheral Blood by Septin 9 DNA Methylation Assay. PLoS ONE 3(11): e3759. doi:10.1371/journal.pone.0003759, 2008

Herranz and Esteller, DNA methylation and histone modifications in subjects with cancer: potential prognostic and therapeutic targets. Methods Mol Biol. 361:25-62, 2007

Hervouet et al, Disruption of Dnmt1/PCNA/UHRF1 Interactions Promotes Tumorigenesis from Human and Mice Glial Cells PLoS ONE 5(6): e11333. doi:10.1371/journal.pone.0011333, 2010

Holdenrieder et al, Nucleosomes in serum of subjects with benign and malignant diseases. Int. J. Cancer (Pred. Oncol.): 95, 114-120, 2001

*Holdenrieder et al, Nucleosomes in Serum as a Marker for Cell Death. Clin Chem Lab Med; 39(7), 596-605, 2001

Holdenrieder et al, Cell-Free DNA in Serum and Plasma: Comparison of ELISA and Quantitative PCR. Clinical Chemistry: 51(8), 1544-1546, 2005.

Holdenrieder and Stieber, Clinical use of circulating nucleosomes. Critical Reviews in Clinical Laboratory Sciences; 46(1): 1-24, 2009

Ricke and Bielinsky, Easy detection of chromatin binding proteins by the histone association assay. Biol Proced Online; 7(1), 60-69, 2005

Rodriguez-Paredes and Esteller, Cancer epigenetics reaches mainstream oncology. Nature Medicine: 17(3), 330-339, 2011

Salgame et al, An ELISA for detection of apoptosis. Nucleic Acids Research, 25(3), 680-681, 1997

Sims et al, HMGB1 and RAGE in inflammation and cancer. Annu. Rev. Immunol. 28, 367-388, 2010

Stoetzer et al, Circulating nucleosomes and biomarkers of immunogenic cell death as predictive and prognostic markers in cancer patients undergoing cytotoxic therapy. Expert Opin Biol Ther. 12(Suppl. 1): S217-S224, 2012

Tang et al, High-mobility Group Box 1 [HMGB1] and Cancer. Biochim Biophys Acta. 1799(1-2) 131, 2010

Urbonaviciute et al, Induction of inflammatory and immune responses by HMGB1-nucleosome complexes: implications for the pathogenesis of SLE. J Exp Med, 205(13), 3007-3018, 2008

Urbonaviciute and Voll, High-mobility group box 1 represents a potential marker of disease and novel therapeutic target in systemic lupus erythematosus. J Internal Medicine, 270, 309-318, 2011 van Nieuwenhuijze et al, Time between onset of apoptosis and release of nucleosomes from apoptotic cells: putative implications for systemic lupus erythematosus. Ann Rheum Dis; 62: 10-14, 2003

Yoshida and Shimura, Isolation of nonhistone chromosomal protein from calf thymus. Biochimica et Biophysica Acta (BBA)—Protein Structure; 263(3), 690-695, 1972

The invention claimed is:

1. A method for detecting the presence of a nucleosome-protein adduct in a sample, wherein the nucleosome-protein adduct includes a chromatin modifying enzyme, a nuclear receptor or a hormone, which comprises the steps of:
   (i) contacting the sample with a first binding agent which binds to nucleosomes or a component thereof;
   (ii) contacting the nucleosomes or sample with a second binding agent which binds to a protein adducted to the nucleosome;
   (iii) detecting or quantifying the binding of said second binding agent to the adducted protein in the sample; and
   (iv) using the presence or degree of such binding as a measure of the presence of nucleosome adducts in the sample.

2. A method for detecting the presence of a nucleosome-protein adduct in a sample, wherein the nucleosome-protein adduct includes a chromatin modifying enzyme, a nuclear receptor or a hormone, which comprises the steps of:
   (i) contacting a sample with a first binding agent which binds to a protein adducted to a nucleosome;
   (ii) contacting the nucleosomes or sample with a second binding agent which binds to nucleosomes or a component thereof;
   (iii) detecting or quantifying the binding of said second binding agent to nucleosomes or a component thereof in the sample; and
   (iv) using the presence or degree of such binding as a measure of the presence of nucleosome adducts in the sample.

3. A method for detecting the presence of a nucleosome-protein adduct in a sample, wherein the nucleosome-protein adduct includes a chromatin modifying enzyme, a nuclear receptor or a hormone, which comprises the steps of:
   (i) contacting the sample with a first binding agent which binds to nucleosomes, a component thereof or a protein adducted to a nucleosome;
   (ii) contacting the nucleosomes or sample with a second binding agent which binds to nucleosomes or a component thereof when the first binding agent binds to the adducted protein, or said second binding agent binds a protein adducted to the nucleosome when the first binding agent binds to nucleosomes or a component thereof;
   (iii) detecting or quantifying the binding of said second binding agent to nucleosomes, a component thereof or the adducted protein in the sample; and
   (iv) using the presence or degree of such binding as a measure of the presence of nucleosome adducts in the sample.

4. The method as defined in claim 3, wherein the chromatin modifying enzyme is EZH2.

5. The method as defined in claim 3, wherein the nuclear receptor is an estrogen receptor, androgen receptor, progesterone receptor, thyroid hormone receptor or retinoic acid receptor.

6. The method as defined in claim 3, wherein the nuclear receptor is additionally bound to a hormone which is selected from a thyroid hormone, a glucocorticoid hormone or a steroid hormone including an estrogen, an androgen, a progestogen or retinoic acid.

7. The method as defined in claim 3, wherein the nucleosome or nucleosome component binder is directed to bind to a particular epigenetic signal structure such that only a particular subset of nucleosome adducts containing said epigenetic signal structure are detected.

8. The method as defined in claim 3, wherein the binding agent is an antibody, an antibody fragment or an aptamer.

9. The method as defined in claim 3, wherein the sample is a biological fluid.

10. A method as defined in claim 3, wherein the sample is blood or serum or plasma.

11. A method for detecting the presence of a nucleosome-protein adduct as defined in claim 3, in a cell which comprises the steps of:
    (i) isolating chromatin from a cell;
    (ii) digesting, sonicating or otherwise breaking down the chromatin to form mono-nucleosomes and/or oligo-nucleosomes; and
    (iii) detecting or measuring the presence of the nucleosome adduct as defined in a method of claim 3.

12. A method for detecting or diagnosing a disease status in an animal or a human subject which comprises the steps of:
    (i) detecting or measuring a nucleosome adduct in a body fluid of a subject as defined in the method of claim 3; and
    (ii) using the nucleosome adduct level detected to identify the disease status of the subject.

13. A method for assessment of an animal or a human subject for suitability for a medical treatment which comprises the steps of:

(i) detecting or measuring a nucleosome adduct in a body fluid of the subject as defined in the method of claim 3; and (ii) using the nucleosome adduct level detected as a parameter for selection of a suitable treatment for the subject.

14. A method for monitoring a treatment of an animal or a human subject which comprises the steps of:
(i) detecting or measuring a nucleosome adduct in a body fluid of the subject as defined in the method of claim 3;
(ii) repeating the detection or measurement of a nucleosome adduct in a body fluid of the subject on one or more occasions;
(iii) using any changes in the nucleosome adduct level detected as a parameter for any changes in the condition of the subject.

15. A method as defined in claim 12, wherein the nucleosome adduct is detected or measured as one of a panel of measurements.

16. A method as defined in claim 12, for use in subjects with actual or suspected cancer, benign tumours, inflammatory disease, autoimmune disease, endometriosis, infectious disease, sepsis, stroke or myocardial infarction.

17. A method as defined in claim 3 wherein the nucleosome-protein adduct comprises hormone-hormone receptor-nucleosome complex adducts.

18. The method as defined in claim 17, wherein the hormone-hormone receptor-nucleosome complex adducts comprise a thyroxine-thyroid hormone receptor-nucleosome complex adduct, a triiodothyronine-thyroid hormone receptor-nucleosome complex adduct, a retinoic acid-retinoic acid receptor-nucleosome complex adduct, an androgen-androgen receptor-nucleosome complex adduct or an estrogen-estrogen receptor-nucleosome complex adduct.

19. The method as defined in claim 17, which comprises an antibody or other binder directed to bind to the hormone.

20. The method as defined in claim 17, which comprises the step of extracting the hormone from an antibody captured hormone-hormone receptor-nucleosome complex adduct followed by a quantification step.

21. A method for identifying a nucleosome-protein adduct biomarker for detecting or diagnosing a disease status in an animal or a human subject which comprises the steps of:
(i) detecting or measuring a nucleosome adduct in a body fluid of the subject as defined in the method of claim 3;
(ii) detecting or measuring a nucleosome adduct in a body fluid of a healthy subject or a control subject; and
(iii) using the difference between the levels detected in diseased and control subjects to identify whether a nucleosome adduct is useful as a biomarker for the disease status.

* * * * *